United States Patent
Decker et al.

(10) Patent No.: US 11,781,178 B2
(45) Date of Patent: Oct. 10, 2023

(54) METHODS AND COMPOSITIONS FOR THE AMPLIFICATION OF MRNA

(71) Applicant: BAYLOR COLLEGE OF MEDICINE, Houston, TX (US)

(72) Inventors: William K. Decker, Houston, TX (US); Vanaja Konduri, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 122 days.

(21) Appl. No.: 16/772,682

(22) PCT Filed: Dec. 17, 2018

(86) PCT No.: PCT/US2018/066051
§ 371 (c)(1),
(2) Date: Jun. 12, 2020

(87) PCT Pub. No.: WO2019/118978
PCT Pub. Date: Jun. 20, 2019

(65) Prior Publication Data
US 2020/0308638 A1 Oct. 1, 2020

Related U.S. Application Data

(60) Provisional application No. 62/599,472, filed on Dec. 15, 2017.

(51) Int. Cl.
*C12Q 1/6853* (2018.01)
*C12N 15/10* (2006.01)

(52) U.S. Cl.
CPC ....... *C12Q 1/6853* (2013.01); *C12N 15/1096* (2013.01); *C12Q 2521/107* (2013.01)

(58) Field of Classification Search
CPC ............ C12Q 1/6853; C12Q 2521/107; C12N 15/1096
See application file for complete search history.

(56) References Cited

U.S. PATENT DOCUMENTS

| | | | |
|---|---|---|---|
| 5,962,271 | A | 10/1999 | Chenchik et al. |
| 6,518,019 | B2 | 2/2003 | Gerard et al. |
| 8,728,806 | B2 | 5/2014 | Decker et al. |
| 2005/0074804 | A1 | 4/2005 | Wang et al. |
| 2007/0248578 | A1 | 10/2007 | Tcherepanova et al. |
| 2011/0301223 | A1 | 12/2011 | Broglie et al. |
| 2012/0297504 | A1 | 11/2012 | Granevitze et al. |
| 2015/0064756 | A1* | 3/2015 | Rajagopalan ............ C12P 7/24 435/189 |
| 2015/0152409 | A1 | 6/2015 | Seitz et al. |
| 2020/0308638 | A1 | 10/2020 | Decker et al. |

FOREIGN PATENT DOCUMENTS

| | | |
|---|---|---|
| CN | 101377021 | 3/2009 |
| CN | 101932339 | 12/2010 |
| CN | 103153338 | 6/2013 |
| WO | WO-2005052128 A2 * | 6/2005 ............ A61K 39/00 |
| WO | WO2009/082593 | 7/2009 |
| WO | WO2011/140255 | 11/2011 |
| WO | WO 2016/179475 | 11/2016 |
| WO | WO 2017/173321 | 10/2017 |

OTHER PUBLICATIONS

Palucka (Immunity 39, Jul. 25, 2013, pp. 38-48).*
Gardner ( Trends in Immunology (2016) vol. 37, pp. 855-865).*
Sadeghzadeh ( vol. 254, Aug. 1, 2020, 117580).*
Dunmire (BioTechniques 33:890-896 (Oct. 2002).*
Davoust (Annu. Rev. Immunol. 2000. 18:767-811).*
Database EMBL, "454GmaGlobSeed352667 Soybean Seeds containing globular-stage embryos glycine max cDNA, mRNA sequence," retrieved from EBI accession no. EM_EST:FK618035, Jul. 4, 2008.
Decker et al., "Double Loading of Dendritic Cell MHC Class I and MHC Class II with an AML Antigen Repertoire Enhances Correlates of T-cell Immunity In Vitro via Amplification of T-cell Help," Vaccine, 24:3203-3216, 2006.
Decker, "Th-1 Polarization is Regulated by Dendritic Cell Comparison of MHC Class I and Class II Antigens," Blood, 113:4213-4223, 2009.
Extended European Search Report issued in European Patent Application No. 18888097.5, dated Aug. 4, 2021.
Harris et al., "An improved RNA amplification procedure results in increased yield of autologous RNA transfected dendritic cell-based vaccine," Biochimica et Biophysica Acta, 1724:127-136, 2005.
International Search Report and Written Opinion issued in International Application No. PCT/US2018/066051, dated Mar. 25, 2019.
Konduri, "Modeling Dendritic Cell Vaccination for Influenza Prophylaxis: Potential Applications for Niche Populations," J Infect Dis., 207:1764-1772, 2013.
Markovic et al., "Preparing clinical-grade myeloid dendritic cells by electroporation-mediated transfection of in vitro amplified tumor-derived mRNA and safety testing in stage IV malignant melanoma," J. Translational Med., 4:35, 2006.
Slagter-Jager et al., "Evaluation of RNA amplification methods to improve DC immunotherapy antigen presentation and immune response," Molecular Therapy Nucleic Acids, 2:E91, 2013.
Office Communication issued in corresponding Japanese Application No. 2020-532802, dated Nov. 28, 2022. Machine Translation.
Chen, D, and J T Patton. "Reverse transcriptase adds nontemplated nucleotides to cDNAs during 5'-RACE and primer extension." *BioTechniques* vol. 30,3 (2001): 574-80, 582. doi:10.2144/01303rr02.

(Continued)

*Primary Examiner* — Steven Pohnert
(74) *Attorney, Agent, or Firm* — Parker Highlander PLLC

(57) ABSTRACT

Provided herein are compositions and methods for the synthesis, amplification, and in vitro transcription of full-length cDNA, or cDNA fragments. Methods are provided for reverse transcription of RNA and amplification for in vitro transcription. Further provided are method for loading of dendritic cells with the RNA and homologous lysate for immune stimulation.

13 Claims, 10 Drawing Sheets

Specification includes a Sequence Listing.

(56) References Cited

OTHER PUBLICATIONS

Dörrie, Jan et al. "Therapeutic Cancer Vaccination with Ex Vivo RNA-Transfected Dendritic Cells—An Update." *Pharmaceutics* vol. 12, 2 92. Jan. 23, 2020, doi:10.3390/pharmaceutics12020092.
Fu, Chunmei, and Aimin Jiang. "Dendritic Cells and CD8 T Cell Immunity in Tumor Microenvironment." *Frontiers in immunology* vol. 9 3059. Dec. 20, 2018, doi:10.3389/fimmu.2018.03059.
Gururangan, Sridharan, Elias Sayour, and Duane A. Mitchell. "Total tumor RNA pulsed dendritic cells plus adoptive transfer of ex-vivo enriched autologous T-lymphocytes in the treatment of children with primary brain tumors." *Neuroimmunology and Neuroinflammation* 5 (Oct. 2018): 45.
Liao, Xinsheng et al. "Transfection of RNA encoding tumor antigens following maturation of dendritic cells leads to prolonged presentation of antigen and the generation of high-affinity tumor-reactive cytotoxic T lymphocytes." *Molecular therapy : the journal of the American Society of Gene Therapy* vol. 9,5 (2004): 757-64.
Ponsaerts, P et al. "Cancer immunotherapy using RNA-loaded dendritic cells." *Clinical and experimental immunology* vol. 134,3 (2003): 378-84. doi:10.1046/j.1365-2249.2003.02286.x.
Sabado, Rachel L et al. "Dendritic cell-based immunotherapy." *Cell research* vol. 27,1 (2017): 74-95. doi:10.1038/cr.2016.157.
Sáchez-Paulete, A R et al., "Antigen cross-presentation and T-ceil cross-priming in cancer immunology and immunotherapy," *Annals of oncology : official journal of the European Society for Medical Oncology* vol. 28,suppl_12 (2017): xii44-xii55. doi:10.1093/annonc/mdx237.
Van Nuffel, An M T et al. "Dendritic cells loaded with mRNA encoding full-length tumor antigens prime CD4+ and CD8+ T cells in melanoma patients." *Molecular therapy : the journal of the American Society of Gene Therapy* vol. 20,5 (2012): 1063-74. doi:10.1038/mt.2012.11.
Office Communication issued in corresponding Chinese Application No. 201880087136.7, dated May 12, 2023. Machine Translation.

* cited by examiner ized sequences, as in standard PCR. A third option for the 5'
METHODS AND COMPOSITIONS FOR THE AMPLIFICATION OF MRNA This application is a national phase application under 35 U.S.C. § 371 of International Application No. PCT/US2018/066051, filed Dec. 17, 2018, which claims the benefit of U.S. Provisional Patent Application No. 62/599,472, filed Dec. 15, 2017, the entirety of each of which is incorporated herein by reference.

INCORPORATION OF SEQUENCE LISTING

The sequence listing that is contained in the file named "BACMP0006WO_ST25.txt", which is 1 KB (as measured in Microsoft Windows®) and was created on Dec. 11, 2018, is filed herewith by electronic submission and is incorporated by reference herein.

BACKGROUND OF THE INVENTION

1. Field of the Invention

The present invention relates generally to the field of molecular biology. More particularly, it concerns reverse transcription of mRNA and amplification of those products.

2. Description of Related Art

An important tool in molecular biology is the ability replicate DNA and RNA. DNA can be replicated and amplified in vitro by the polymerase chain reaction, in which primers are hybridized to opposite ends, and opposite strands of a target nucleic acids, and the primers are extended by a DNA dependent DNA polymerase. RNA, which generally exists transiently in vivo, can be reverse transcribed by a RNA dependent DNA polymerase (reverse transcriptase) in order to generate a DNA copy, which is far more stable than RNA. The DNA which is generated from reverse transcription, referred to as complementary DNA or cDNA, can then be amplified, sequenced, transcribed back into RNA, incorporated into a vector for cloning, or any combination thereof.

A variety of methods and enzymes currently exist to reverse transcribe RNA into DNA. Frequently, when designing primers for cDNA synthesis from mRNA templates, researchers take advantage of the poly(A) tail which exists on the 3' end of mRNA. This allows researchers to use primers with a poly(T) sequence at the 3' end of the primer, and makes capturing 3' sequence information from mRNA very simple. The second primer, corresponding to the 5' end of the target sequence, comprises either random or targeted sequences, as in standard PCR. A third option for the 5' primer is to take advantage of the inherent template switching activity of some reverse transcriptase enzymes and hybridize the second primer to a polynucleotide overhang generated by the reverse transcriptase, and continue to synthesize the strand complementary to the second primer (see, for example, U.S. Pat. No. 5,962,271). The complementary DNA strand can then be copied using a standard PCR reaction to amplify the sequence. The primers used in cDNA synthesis and amplification may include a promoter so that the cDNA can be transcribed using a process of in vitro transcription to generate large quantities of target mRNA. RNA generated by in vitro transcription can then be used to induce antigen presentation on dendritic cells. The methods for reverse transcription and in vitro transcription, however, suffer from high bias during the reverse transcription process, and inefficient in vitro transcription, demonstrating a need for improved methods and compositions to enhance these processes.

SUMMARY OF THE INVENTION

In a first embodiment, there is provided an oligonucleotide comprising the sequence of SEQ ID NO: 1. In some aspects, the oligonucleotide is further defined as a primer. In certain aspects, the oligonucleotide comprises less than 40 nucleotides. In a specific aspect, the oligonucleotide consists of SEQ ID NO: 1.

In a further embodiment, there is provided a composition comprising a first primer and a second primer, wherein the first primer comprises a nucleic acid sequence of SEQ ID NO: 1, and wherein the second primer comprises a nucleic acid sequence of SEQ ID NO: 2. In several aspects, the composition is further defined as a nucleic acid amplification reaction mixture. In other aspects, the composition further comprises a third primer, wherein the third primer comprises a nucleic acid sequence of SEQ ID NO: 3.

In yet a further embodiment, there is provided a method of synthesizing a first cDNA strand from a template mRNA comprising the steps of: a) hybridizing a first primer to the template mRNA, wherein the first primer comprises a nucleic acid sequence of SEQ ID NO: 2; b) extending the first primer with a reverse transcriptase that has terminal transferase and template switching activity to generate a partial first cDNA strand with an oligo(C) overhang; c) hybridizing a second primer to the oligo(C) overhang of the partial first cDNA strand, wherein the second primer comprises a nucleic acid sequence of SEQ ID NO: 1; and d) extending the partial first cDNA strand from the oligo(C) overhang using the second primer as the template, thereby generating a first cDNA strand. In some aspects, the method further comprises steps e) separating the template mRNA and first cDNA strand; f) hybridizing a third primer to the first cDNA strand; and g) extending the third primer to generate a second cDNA strand, thereby generating a double stranded cDNA. In certain aspects, the second primer comprises a nucleic acid sequence of SEQ ID NO: 1. In several aspects, the third primer comprises a nucleic acid sequence of SEQ ID NO: 3. In further aspects, the template mRNA is obtained from a sample. In some specific aspects, the sample is a tumor sample. In certain specific aspects, the tumor sample is stored in an RNA stabilization solution after removal from a subject. In still further aspects, the RNA stabilization solution is RNALATER®.

In additional aspects, the method further comprises synthesizing RNA from the double stranded cDNA. In some aspects, the synthesizing RNA from the double stranded cDNA comprises in vitro transcription. In more specific aspects, the in vitro transcription comprises adding a fourth primer, a fifth primer, and an RNA polymerase, and synthesizing RNA from the double stranded cDNA with the RNA polymerase. In a particular aspect, the fourth primer comprises a nucleic acid sequence of SEQ ID NO: 1. In a further aspect, the fourth primer comprises a nucleic acid sequence of SEQ ID NO: 3. In another aspect, the method further comprises capping the RNA.

In certain aspects, the method further comprises amplifying the double stranded cDNA. In some aspects, the second primer comprises the nucleic acid sequence of SEQ ID NO: 1. In other aspects, the third primer comprises the nucleic acid sequence of SEQ ID NO: 3. In particular aspects, amplifying the double stranded cDNA comprises adding a DNA dependent DNA polymerase, a fourth primer, and a fifth primer and amplifying the cDNA by polymerase chain reaction. In some specific aspects, the fourth primer comprises the nucleic acid sequence of SEQ ID NO: 1. In another aspect, the fifth primer comprises the nucleic acid sequence of SEQ ID NO: 3.

In further aspects, the method additionally comprises in vitro transcribing the amplified cDNA to generate sense-strand amplified mRNA. In several aspects, the second primer comprises the nucleic acid sequence of SEQ ID NO: 1. In certain aspects, the third primer comprises the nucleic acid sequence of SEQ ID NO: 3. In some additional aspects, the in vitro transcribing of the amplified cDNA comprises adding primers having the sequence of SEQ ID NO: 1 and SEQ ID NO: 3 to the amplified cDNA, and hybridizing said primers to the amplified cDNA. In a particular aspect, the in vitro transcribing of the amplified cDNA comprises adding an RNA polymerase to the amplified cDNA, and extending the hybridized primers to generate RNA. In another aspect, the method further comprises capping the amplified RNA.

A further embodiment of the invention provides, a method for transducing a dendritic cell population comprising contacting the dendritic cell population with a nucleic acid encoding one or more antigens, wherein the nucleic acid comprises RNA generated by any of the methods and aspects described above. In some aspects, the method further comprises contacting the dendritic cell population with a tumor cell lysate. In another aspect, the tumor cell lysate comprises a tumor antigen with an epitope having a sequence that overlaps a minimum of 5 amino acids with the sequence of the nucleic acid encoding one or more antigens.

In yet a further embodiment, there is provided a method for providing an immune response in a subject having a diseased cell population comprising: a) obtaining a primed dendritic cell population produced by the method according to claim 36 or 37; and b) administering an effective amount of the primed dendritic cell population to the subject. In certain aspects, the antigen-primed dendritic cell has been primed with an antigen associated with a cancer, an autoimmune disease or an infectious disease. In several aspects, the antigen-primed dendritic cell has been primed with at least one tumor antigen. In additional aspects, the method further comprises administering an immune checkpoint inhibitor. In another aspect, the immune checkpoint inhibitor is a CTLA-4 antagonist. In certain aspects, the immune checkpoint inhibitor is ipilimumab, pembrolizumab or nivolumab.

Still yet a further embodiment of the invention provides a kit comprising an oligonucleotide primer of claim 1, an oligonucleotide primer of SEQ ID NO:2 and/or an oligonucleotide primer of SEQ ID NO:3. In some aspects, the kit may additionally comprise nucleic acids isolated from cancer cells, a DNA polymerase, and/or an RNA stabilization solution. In a particular aspect, the RNA stabilization solution is RNALATER®. In another aspect, the kit is further defined as a cDNA synthesis kit. In additional aspects, the kit further comprises dNTPs, MgCl$_2$, reverse transcriptase, and/or RNase inhibitor.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
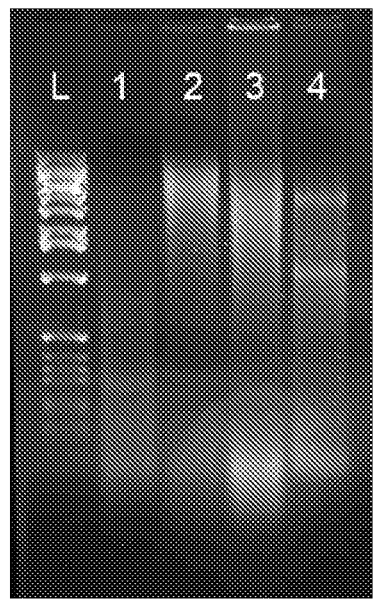
FIG. 1: Freshly harvested tumor samples yield better quality RNA than frozen archived samples. Pictured, RNA isolated from either frozen or fresh tumor tissue was run on a non-denaturing 1% agarose gel. From left to right: L: ladder; 1: frozen tumor sample RNA; 2 frozen tumor sample RNA; 3: Frozen tumor sample RNA; 4: Fresh tumor sample RNA.

Reverse transcription is a process in which a RNA dependent DNA polymerase synthesizes DNA using RNA as a template, and has become increasingly important as a tool in molecular biology for understanding gene expression and sequencing cellular RNA. Using a process of in vitro transcription and amplification following reverse transcription allows for the production of large quantities of RNA from a template RNA. However, there is a need for methods to decrease the bias and increase the efficiency of the reverse transcription process.

Accordingly, in certain embodiments, the present disclosure provides methods for decreasing the bias of the reverse transcription process, and provides methods for increasing amplification efficiency of the reverse transcribed molecules. In particular, the present studies found the nucleotide composition and sequence of the primers to be important to the reverse transcription process, as well as the incorporation of a promoter sequence in the primers, for efficient in vitro transcription.

Specifically, some embodiments provide compositions and methods for the synthesis, amplification, and in vitro transcription of full-length cDNA, or cDNA fragments. The method may comprise contacting RNA with a primer which can anneal to the poly(A) tail of mRNA, a suitable enzyme which possesses reverse transcriptase activity, and a template switching oligonucleotide under conditions sufficient to permit the template-dependent extension of the primer a cDNA complementary to the mRNA template. The template switching oligonucleotide can hybridize to a reverse transcriptase generated overhang at the 3' end of the newly generated cDNA, and allow for the reverse transcriptase to continue to synthesize the complement of the template switching oligonucleotide on the 3' end of the cDNA. Subsequent amplification can introduce a promoter sequence for in vitro transcription. In vitro transcribed RNA can then be loaded into dendritic cells with homologous lysate for immune stimulation. Thus, further embodiments provide methods for loading of dendritic cells and use of the dendritic cell vaccine for the treatment of diseases, such as cancer.

II. DEFINITIONS

"Amplification," as used herein, refers to an in vitro process for increasing the number of copies of a nucleotide sequence or sequences. Nucleic acid amplification results in the incorporation of nucleotides into DNA or RNA. As used herein, one amplification reaction may consist of many rounds of DNA replication. For example, one PCR reaction may consist of 30-100 "cycles" of denaturation and replication.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, PCR: A Practical Approach and PCR2: A Practical Approach (IRL Press, Oxford, 1991 and 1995, respectively).

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

"Incorporating," as used herein, means becoming part of a nucleic acid polymer.

The term "in the absence of exogenous manipulation" as used herein refers to there being modification of a nucleic acid molecule without changing the solution in which the nucleic acid molecule is being modified. In specific embodiments, it occurs in the absence of the hand of man or in the absence of a machine that changes solution conditions, which may also be referred to as buffer conditions. However, changes in temperature may occur during the modification.

A "nucleoside" is a base-sugar combination, i.e., a nucleotide lacking a phosphate. It is recognized in the art that there is a certain inter-changeability in usage of the terms nucleoside and nucleotide. For example, the nucleotide deoxyuridine triphosphate, dUTP, is a deoxyribonucleoside triphosphate. After incorporation into DNA, it serves as a DNA monomer, formally being deoxyuridylate, i.e., dUMP or deoxyuridine monophosphate. One may say that one incorporates dUTP into DNA even though there is no dUTP moiety in the resultant DNA. Similarly, one may say that one incorporates deoxyuridine into DNA even though that is only a part of the substrate molecule.

"Nucleotide," as used herein, is a term of art that refers to a base-sugar-phosphate combination. Nucleotides are the monomeric units of nucleic acid polymers, i.e., of DNA and RNA. The term includes ribonucleotide triphosphates, such as rATP, rCTP, rGTP, or rUTP, and deoxyribonucleotide triphosphates, such as dATP, dCTP, dUTP, dGTP, or dTTP.

The term "nucleic acid" or "polynucleotide" will generally refer to at least one molecule or strand of DNA, RNA, DNA-RNA chimera or a derivative or analog thereof, comprising at least one nucleobase, such as, for example, a naturally occurring purine or pyrimidine base found in DNA (e.g., adenine "A," guanine "G," thymine "T" and cytosine "C") or RNA (e.g., A, G, uracil "U" and C). The term "nucleic acid" encompasses the terms "oligonucleotide" and "polynucleotide." "Oligonucleotide," as used herein, refers collectively and interchangeably to two terms of art, "oligonucleotide" and "polynucleotide." Note that although oligonucleotide and polynucleotide are distinct terms of art, there is no exact dividing line between them and they are used interchangeably herein. The term "adaptor" may also be used interchangeably with the terms "oligonucleotide" and "polynucleotide." In addition, the term "adaptor" can indicate a linear adaptor (either single stranded or double stranded) or a stem-loop adaptor. These definitions generally refer to at least one single-stranded molecule, but in specific embodiments will also encompass at least one additional strand that is partially, substantially, or fully complementary to at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss," and a double-stranded nucleic acid by the prefix "ds."

"Oligonucleotide," as used herein, refers collectively and interchangeably to two terms of art, "oligonucleotide" and "polynucleotide." Note that although oligonucleotide and polynucleotide are distinct terms of art, there is no exact dividing line between them and they are used interchangeably herein. The term "adaptor" may also be used interchangeably with the terms "oligonucleotide" and "polynucleotide."

A "nucleic acid molecule" or "nucleic acid target molecule" refers to any single-stranded or double-stranded nucleic acid molecule including standard canonical bases, hypermodified bases, non-natural bases, or any combination of the bases thereof. For example and without limitation, the nucleic acid molecule contains the four canonical DNA bases—adenine, cytosine, guanine, and thymine, and/or the four canonical RNA bases—adenine, cytosine, guanine, and uracil. Uracil can be substituted for thymine when the nucleoside contains a 2'-deoxyribose group. The nucleic acid molecule can be transformed from RNA into DNA and from DNA into RNA. For example, and without limitation, mRNA can be created into complementary DNA (cDNA) using reverse transcriptase and DNA can be created into RNA using RNA polymerase. A nucleic acid molecule can be of biological or synthetic origin. Examples of nucleic acid molecules include genomic DNA, cDNA, RNA, a DNA/RNA hybrid, amplified DNA, a pre-existing nucleic acid library, etc. A nucleic acid may be obtained from a human sample, such as blood, serum, plasma, cerebrospinal fluid, cheek scrapings, biopsy, semen, urine, feces, saliva, sweat, etc. A nucleic acid molecule may be subjected to various treatments, such as repair treatments and fragmenting treatments. Fragmenting treatments include mechanical, sonic, and hydrodynamic shearing. Repair treatments include nick repair via extension and/or ligation, polishing to create blunt ends, removal of damaged bases, such as deaminated, derivatized, abasic, or crosslinked nucleotides, etc. A nucleic acid molecule of interest may also be subjected to chemical modification (e.g., bisulfite conversion, methylation/demethylation), extension, amplification (e.g., PCR, isothermal, etc.), etc.

"Analogous" forms of purines and pyrimidines are well known in the art, and include, but are not limited to aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxyuracil, 2-methylthio-$N^6$-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. The nucleic acid molecule can also contain one or more hypermodified bases, for example and without limitation, 5-hydroxymethyluracil, 5-hydroxyuracil, α-putrescinylthymine, 5-hydroxymethylcytosine, 5-hydroxycytosine, 5-methylcytosine, $N^4$-methyl cytosine, 2-aminoadenine, α-carbamoylmethyladenine, $N^6$-methyladenine, inosine, xanthine, hypoxanthine, 2,6-diaminpurine, and $N^7$-methylguanine. The nucleic acid molecule can also contain one or more non-natural bases, for example and without limitation, 7-deaza-7-hydroxymethyl adenine, 7-deaza-7-hydroxymethylguanine, isocytosine (isoC), 5-methylisocytosine, and isoguanine (isoG). The nucleic acid molecule containing only canonical, hypermodified, non-natural bases, or any combinations the bases thereof, can also contain, for example and without limitation where each linkage between nucleotide residues can consist of a standard phosphodiester linkage, and in addition, may contain one or more modified linkages, for example and without limitation, substitution of the non-bridging oxygen atom with a nitrogen atom (i.e., a phosphoramidate linkage, a sulfur atom (i.e., a phosphorothioate linkage), or an alkyl or aryl group (i.e., alkyl or aryl phosphonates), substitution of the bridging oxygen atom with a sulfur atom (i.e., phosphorothiolate), substitution of the phosphodiester bond with a peptide bond (i.e., peptide nucleic acid or PNA), or formation of one or more additional covalent bonds (i.e., locked nucleic acid or LNA), which has an additional bond between the 2'-oxygen and the 4'-carbon of the ribose sugar.

Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" may refer to nucleic acid(s) that are substantially complementary, as may be assessed by the same nucleotide comparison set forth above. The term "substantially complementary" may refer to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double-stranded nucleic acid molecule during hybridization. In certain embodiments, the term "substantially complementary" refers to at least one nucleic acid that may hybridize to at least one nucleic acid strand or duplex in stringent conditions. In certain embodiments, a "partially complementary" nucleic acid comprises at least one sequence that may hybridize in low stringency conditions to at least one single or double-stranded nucleic acid, or contains at least one sequence in which less than about 70% of the nucleobase sequence is capable of base-pairing with at least one single or double-stranded nucleic acid molecule during hybridization.

The term "non-complementary" refers to nucleic acid sequence that lacks the ability to form at least one Watson-Crick base pair through specific hydrogen bonds.

The term "blunt end" as used herein refers to the end of a dsDNA molecule having 5' and 3' ends, wherein the 5' and 3' ends terminate at the same nucleotide position. Thus, the blunt end comprises no 5' or 3' overhang.

The term "overhang" as used herein refers to the end of a dsDNA molecule having 5' and 3' ends, wherein the 5' and 3' ends terminate at different nucleotide positions, leaving at least one nucleotide on the end of either the 5' and 3' end which has no nucleotide to hydrogen bond with.

The term "cap" as used herein is a guanine nucleoside that is joined via its 5'-carbon to a triphosphate group that is, in turn, joined to the 5'-carbon of the most 5'-nucleotide of the primary mRNA transcript, and in most eukaryotes, the nitrogen at the 7 position of guanine in the cap nucleotide is methylated. Most eukaryotic cellular mRNA transcripts and most eukaryotic viral mRNA transcripts are blocked or "capped" at their 5' terminus. In addition to mRNA, some other forms of eukaryotic RNA, such as but not limited to, small nuclear RNA ("snRNA") and pre-micro RNA (i.e. "pre-miRNA", the primary transcripts that are processed to miRNA) are also capped. The 5' caps of eukaryotic cellular and viral mRNAs (and some other forms of RNA) play important roles in RNA stability and processing. For example, the cap is required to varying degrees for processing and maturation of an RNA transcripts in the nucleus, transport of mRNA from the nucleus to the cytoplasm, mRNA stability, and efficient translation of the mRNA to protein.

"Sample" means a material obtained or isolated from a fresh or preserved biological sample or synthetically-created source that contains nucleic acids of interest. In certain embodiments, a sample is the biological material that contains the variable immune region(s) for which data or information are sought. Samples can include at least one cell, fetal cell, cell culture, tissue specimen, blood, serum, plasma, saliva, urine, tear, vaginal secretion, sweat, lymph fluid, cerebrospinal fluid, mucosa secretion, peritoneal fluid, ascites fluid, fecal matter, body exudates, umbilical cord blood, chorionic villi, amniotic fluid, embryonic tissue, multicellular embryo, lysate, extract, solution, or reaction mixture suspected of containing immune nucleic acids of interest. Samples can also include non-human sources, such as non-human primates, rodents and other mammals, other animals, plants, fungi, bacteria, and viruses.

As used herein in relation to a nucleotide sequence, "substantially known" refers to having sufficient sequence information in order to permit preparation of a nucleic acid molecule, including its amplification. This will typically be about 100%, although in some embodiments some portion of an adaptor sequence is random or degenerate. Thus, in specific embodiments, substantially known refers to about 50% to about 100%, about 60% to about 100%, about 70% to about 100%, about 80% to about 100%, about 90% to about 100%, about 95% to about 100%, about 97% to about 100%, about 98% to about 100%, or about 99% to about 100%.

III. NUCLEIC ACIDS OF THE EMBODIMENTS

Nucleic acids of the present disclosure can comprise amplification, reverse transcription, and/or in vitro transcription primers and oligonucleotides, tumor derived nucleic acids and/or recombinant nucleic acids encoding one or more proteins or peptides, such as those which may induce an immune response that is effective against a tumor or tumor cell. In some embodiments, generation of nucleic acids which may induce an immune response comprises reverse transcription of target mRNA to generate cDNA. Methods of reverse transcription are well known in the art (U.S. Pat. Nos. 5,962,271 and 6,518,019, incorporated herein by reference). Reverse transcription is performed by a RNA dependent DNA polymerase, also known as a reverse transcriptase. The reverse transcriptase binds to a primer hybridized to the 3' end of a target mRNA, and synthesizes DNA complementary to the mRNA. The reverse transcriptase may add several non-templated nucleotides to the 3' end of the newly synthesized cDNA, such as a short poly(C) tail. A second primer may be hybridized to the 3' end of the nascent cDNA, and the reverse transcriptase may continue synthesizing DNA complementary to the primer, using its template switch activity to use the second primer as its template.

The primers or oligonucleotides used in reverse transcription or amplification may allow for the addition of exogenous DNA or RNA sequence to the 5' and 3' ends of the target sequences during complementary strand synthesis. The primers or oligonucleotides used for priming the reverse transcription or amplification reactions may incorporate a variety of features including, but not limited to transcriptional promoters, ribosomal binding sites, or restriction endonuclease cleavage sites. In some embodiments, a primer may include a transcriptional promoter sequence.

cDNA prepared by reverse transcription can be amplified or transcribed to RNA. cDNAs may be amplified by PCR, to increase the concentration of the cDNA. The primers for reverse transcription may be used as the primers for PCR, or separate primers may be added. The PCR reaction may utilize the reverse transcriptase in order to amplify the cDNA, or a DNA dependent DNA polymerase may be added to increase the efficiency of DNA amplification. The primers for reverse transcription or DNA amplification may include transcription promoter sequences, such as the T7 promoter sequence. cDNA or amplified cDNA may be transcribed in an in vitro transcription process to generate large quantities of the initial target RNA using any commercially available RNA polymerase or in vitro transcription kit, such as AMPLISCRIBE™ T7-FLASH™ (LUCIGEN® Cat. No. ASF3257).

In certain embodiments a nucleic acid composition contains both a tumor derived nucleic acid population and a recombinant nucleic acid component. This combination nucleic acid composition increases the prevalence of certain known tumor antigens or other nucleic acids encoding proteins or peptides that enhance the effectiveness of the methods and compositions described herein.

A "tumor-derived" nucleic acid refers to a nucleic acid that has its origin in a tumor cell, and which includes RNA corresponding to a tumor antigen(s). Included is RNA that encodes all or a portion of a tumor antigen or a previously identified tumor antigen. Such nucleic acid can be "in vitro transcribed," e.g., reverse transcribed to produce cDNA that can be amplified by PCR and subsequently be transcribed in vitro, with or without cloning the cDNA. Also included is RNA that is provided as a fractionated preparation of tumor cell. Because even unfractionated RNA preparation (e.g., total RNA or total poly A RNA) can be used, it is not necessary that a tumor antigen be identified. In one embodiment, the preparation is fractionated with respect to a non-RNA component(s) of the cell in order to decrease the concentration of a non-RNA component, such as protein, lipid, and/or DNA and enrich the preparation for RNA. If desired, the preparation can be further fractionated with respect to the RNA (e.g., by subtractive hybridization) such that "tumor-specific" or "pathogen-specific" RNA is produced.

By "tumor-specific" RNA is meant an RNA sample that, relative to unfractionated tumor-derived RNA, has a high content of RNA that is preferentially present in a tumor cell compared with a non-tumor cell. For example, tumor-specific RNA includes RNA that is present in a tumor cell, but not present in a non-tumor cell. Also encompassed in this definition is an RNA sample that includes RNA that is present both in tumor and non-tumor cells, but is present at a higher level in tumor cells than in non-tumor cells. Also included within this definition is RNA that encodes a previously identified tumor antigen and which is produced in vitro, e.g., from a plasmid or by PCR. Alternatively, tumor-specific RNA can be prepared by fractionating an RNA sample such that the percentage of RNA corresponding to a tumor antigen is increased, relative to unfractionated tumor-derived RNA. For example, tumor-specific RNA can be prepared by fractionating tumor-derived RNA using conventional subtractive hybridization techniques against RNA from non-tumor cells.

Methods suitable for producing tumor-derived nucleic acid or RNA are provided herein. These nucleic acids can be used for priming dendritic cells, and in the preparation of mature dendritic cells. It is not necessary that the nucleic acid be provided to the DC in a purified form. Preferably, the RNA sample (i.e., the fractionated tumor preparation) is at least 50%, 60%, 70%, 75%, 80%, 85%, 90%, 91%, 92%, 93%, 94%, 95%, 96%, 97%, 98% or even 99% RNA (wt/vol).

Art-known transfection methods are suitable for introducing the tumor-derived nucleic acid into a dendritic cell. For example, 5-50 µg of RNA in 500 µl of Opti-MEM can be mixed with a cationic lipid at a concentration of 10 to 100 and incubated at room temperature for 20 to 30 minutes. Other suitable lipids include LIPOFECTIN™ (1:1 (w/w) DOTMA:DOPE), LIPOFECTAMINE™ (3:1 (w/w) DOSPA:DOPE), DODAC:DOPE (1:1), CHOL:DOPE (1:1), DMEDA, CHOL, DDAB, DMEDA, DODAC, DOPE, DORI, DORIE, DOSPA, DOTAP, and DOTMA. The resulting RNA-lipid complex is then added to 1-3×106 cells, preferably 2×106, antigen-presenting cells in a total volume of approximately 2 ml (e.g., in Opti-MEM), and incubated at 37° C. for 2 to 4 hours. Alternatively, the RNA can be introduced into the antigen presenting cells by employing conventional techniques, such as electroporation or calcium phosphate transfection with 1-5×106 cells and 5 to 50 µg of RNA. Typically, 5-20 µg of poly A RNA or 25-50 µg of total RNA are typically used.

When the RNA is provided as a tumor preparation, the preparation typically is fractionated or otherwise treated to decrease the concentration of proteins, lipids, and/or DNA in the preparation, and enrich the preparation for RNA. For example, art-known RNA purification methods can be used to at least partially purify the RNA from the tumor cell or pathogen. It is also acceptable to treat the RNA preparation with proteases or RNase-free DNases.

IV. DENDRITIC CELL POPULATIONS OF THE EMBODIMENTS

Methods for isolating culturing and priming dendritic cells are well known in the art. For example, U.S. Pat. No. 8,728,806, which is incorporated herein by reference in its entirety, provides detailed methods for providing antigen primed dendritic cells that may be used in the compositions and methods of the embodiments. In certain aspects, dendritic cells for use according to the embodiments are isolated from a subject that is to be treated by a method of the embodiments. In other aspects, dendritic cells may be from a different subject, such as an HLA-matched donor. In certain aspects, the dendritic cells are from a bank of dendritic cells having a defined HLA typing. In preferred aspects, primed dendritic cells for use according to the embodiments are homologously-loaded with antigen as detailed herein and in U.S. Pat. No. 8,728,806.

Methods for isolating cell populations enriched for dendritic cell precursors and immature dendritic cells from various sources, including blood and bone marrow, are known in the art. For example, dendritic cell precursors and immature dendritic cells can be isolated by collecting heparinized blood, by apheresis or leukapheresis, by preparation of buffy coats, rosetting, centrifugation, density gradient centrifugation (e.g., using Ficoll (such as FICOLL-PAQUE®), PERCOLL® (colloidal silica particles (15-30 mm diameter) coated with non-dialyzable polyvinylpyrrolidone (PVP)), sucrose, and the like), differential lysis of cells, filtration, and the like. In certain embodiments, a leukocyte population can be prepared, such as, for example, by collecting blood from a subject, defibrinating to remove the platelets and lysing the red blood cells. Dendritic cell precursors and immature dendritic cells can optionally be enriched for monocytic dendritic cell precursors by, for example, centrifugation through a PERCOLL® gradient. In other aspects, dendritic cell precursors can be selected using CD14 selection of G-CSF mobilized peripheral blood.

Dendritic cell precursors and immature dendritic cells optionally can be prepared in a closed, aseptic system. As used herein, the terms "closed, aseptic system" or "closed system" refer to a system in which exposure to non-sterilize, ambient, or circulating air or other non-sterile conditions is minimized or eliminated. Closed systems for isolating dendritic cell precursors and immature dendritic cells generally exclude density gradient centrifugation in open top tubes, open air transfer of cells, culture of cells in tissue culture plates or unsealed flasks, and the like. In a typical embodiment, the closed system allows aseptic transfer of the dendritic cell precursors and immature dendritic cells from an initial collection vessel to a sealable tissue culture vessel without exposure to non-sterile air.

In certain embodiments, monocytic dendritic cell precursors are isolated by adherence to a monocyte-binding substrate. For example, a population of leukocytes (e.g., isolated by leukapheresis) can be contacted with a monocytic dendritic cell precursor adhering substrate. When the population of leukocytes is contacted with the substrate, the monocytic dendritic cell precursors in the leukocyte population preferentially adhere to the substrate. Other leukocytes (including other potential dendritic cell precursors) exhibit reduced binding affinity to the substrate, thereby allowing the monocytic dendritic cell precursors to be preferentially enriched on the surface of the substrate.

Suitable substrates include, for example, those having a large surface area to volume ratio. Such substrates can be, for example, a particulate or fibrous substrate. Suitable particulate substrates include, for example, glass particles, plastic particles, glass-coated plastic particles, glass-coated polystyrene particles, and other beads suitable for protein absorption. Suitable fibrous substrates include microcapillary tubes and microvillous membrane. The particulate or fibrous substrate usually allows the adhered monocytic dendritic cell precursors to be eluted without substantially reducing the viability of the adhered cells. A particulate or fibrous substrate can be substantially non-porous to facilitate elution of monocytic dendritic cell precursors or dendritic cells from the substrate. A "substantially non-porous" substrate is a substrate in which at least a majority of pores present in the substrate are smaller than the cells to minimize entrapping cells in the substrate.

Adherence of the monocytic dendritic cell precursors to the substrate can optionally be enhanced by addition of binding media. Suitable binding media include monocytic dendritic cell precursor culture media (e.g., AIM-V®, RPMI 1640, DMEM, X-VIVO 15®, and the like) supplemented, individually or in any combination, with for example, cytokines (e.g., Granulocyte/Macrophage Colony Stimulating Factor (GM-CSF), Interleukin 4 IL-4), or Interleukin 13 (IL-13)), blood plasma, serum (e.g., human serum, such as autologous or allogenic sera), purified proteins, such as serum albumin, divalent cations (e.g., calcium and/or magnesium ions) and other molecules that aid in the specific adherence of monocytic dendritic cell precursors to the substrate, or that prevent adherence of non-monocytic dendritic cell precursors to the substrate. In certain embodiments, the blood plasma or serum can be heated-inactivated. The heat-inactivated plasma can be autologous or heterologous to the leukocytes.

Following adherence of monocytic dendritic cell precursors to the substrate, the non-adhering leukocytes are separated from the monocytic dendritic cell precursor/substrate complexes. Any suitable means can be used to separate the non-adhering cells from the complexes. For example, the mixture of the non-adhering leukocytes and the complexes can be allowed to settle, and the non-adhering leukocytes and media decanted or drained. Alternatively, the mixture can be centrifuged, and the supernatant containing the non-adhering leukocytes decanted or drained from the pelleted complexes.

Isolated dendritic cell precursors can be cultured ex vivo for differentiation, maturation and/or expansion. (As used herein, isolated immature dendritic cells, dendritic cell precursors, T cells, and other cells, refers to cells that, by human hand, exists apart from their native environment, and are therefore not a product of nature. Isolated cells can exist in purified form, in semi-purified form, or in a non-native environment.) Briefly, ex vivo differentiation typically involves culturing dendritic cell precursors, or populations of cells having dendritic cell precursors, in the presence of one or more differentiation agents. Suitable differentiating agents can be, for example, cellular growth factors (e.g., cytokines such as (GM-CSF), Interleukin 4 (IL-4), Interleukin 13 (IL-13), and/or combinations thereof). In certain embodiments, the monocytic dendritic cells precursors are differentiated to form monocyte-derived immature dendritic cells.

The dendritic cell precursors can be cultured and differentiated in suitable culture conditions. Suitable tissue culture media include AIM-V®, RPMI 1640, DMEM, X-VIVO 15®, and the like. The tissue culture media can be supplemented with serum, amino acids, vitamins, cytokines, such as GM-CSF and/or IL-4, divalent cations, and the like, to promote differentiation of the cells. In certain embodiments, the dendritic cell precursors can be cultured in the serum-free media. Such culture conditions can optionally exclude any animal-derived products. A typical cytokine combination in a typical dendritic cell culture medium is about 500 units/ml each of GM-CSF (50 ng/ml) and IL-4 (10 ng/ml). Dendritic cell precursors, when differentiated to form immature dendritic cells, are phenotypically similar to skin Langerhans cells. Immature dendritic cells typically are CD14– and CD11c+, express low levels of CD86 and CD83, and are able to capture soluble antigens via specialized endocytosis. The immature DC expressed very high levels of CD86. Also, the population was mixed in terms of CD14 and CD11C. Though the majority were CD11c+, there were distinct subpopulations that were CD11c– and CD 14+.

The immature dendritic cells are matured to form mature dendritic cells. Mature DC lose the ability to take up antigen and display up-regulated expression of costimulatory cell surface molecules and various cytokines. Specifically, mature DC express higher levels of MHC class I and II antigens than immature dendritic cells, and mature dendritic cells are generally identified as being CD80+, CD83+, CD86+, and CD14–. Greater MHC expression leads to an increase in antigen density on the DC surface, while up regulation of costimulatory molecules CD80 and CD86 strengthens the T cell activation signal through the counterparts of the costimulatory molecules, such as CD28 on the T cells.

Mature dendritic cells of the present invention can be prepared (i.e., matured) by contacting the immature dendritic cells with effective amounts or concentrations of a nucleic acid composition and a tumor antigen composition. Effective amounts of nucleic acid composition typically range from at most, at least, or about 0.01, 0.1, 1, 5, 10, to 10, 15, 20, 50, 100 ng or mg of nucleic acid per culture dish or per cell, including all values and ranges there between. Effective amounts of tumor antigen composition typically range from at most, at least, or about 0.01, 0.1, 1, 5, 10, to 10, 15, 20, 50, 100 ng or mg of protein per culture dish or per cell. In certain aspects 0.001 ng of tumor antigen/cell to 1 μg of tumor antigen/million cells) can be used. The tumor antigen composition can optionally be heat inactivated or treated (e.g., exposed to protease) prior to contact with dendritic cells. Maturing the immature dendritic cells with a nucleic acid composition and a tumor antigen composition primes the mature dendritic cells for a type 1 (Th-1) response.

The immature DC are typically contacted with effective amounts of a nucleic acid composition and a tumor antigen composition for at most, at least, or about 1, 2, 3, 4, 5, 6, 7, 8, 9, 10, 11, 12, to 10, 11, 12, 13, 14, 15, 16, 17, 18, 19, 20, 21, 22, 23, or 24 minutes, hours, or days. The immature dendritic cells can be cultured and matured in suitable maturation culture conditions. Suitable tissue culture media include AIM-V®, RPMI 1640, DMEM, X-VIVO 15®, and the like. The tissue culture media can be supplemented with amino acids, vitamins, cytokines, such as GM-CSF and/or IL-4, divalent cations, and the like, to promote maturation of the cells.

Maturation of dendritic cells can be monitored by methods known in the art. Cell surface markers can be detected in assays familiar to the art, such as flow cytometry, immunohistochemistry, and the like. The cells can also be monitored for cytokine production (e.g., by ELISA, FACS, or other immune assay). Dendritic cell precursors, immature dendritic cells, and mature dendritic cells, either primed or unprimed, with antigens can be cryopreserved for use at a later date. Methods for cryopreservation are well-known in the art. For example, U.S. Pat. No. 5,788,963, which is incorporated herein by reference in its entirety.

A nucleic acid or nucleic acid primed dendritic cell is a dendritic cell that was incubated or transfected with RNA, e.g., RNA derived from a tumor or tumor cell. Such RNA can be transfected using conventional nucleic acid transfection methods, such as lipid-mediated transfection, electroporation, and calcium phosphate transfection. For example, RNA can be introduced into a DC by incubating the DC with the RNA (or extract) for 1 to 24 hours (e.g., 2 hours) at 37° C.

The nucleic acid-loaded antigen-presenting cells of the present disclosure can be used to stimulate CTL proliferation in vivo or ex vivo. The ability of the nucleic acid-loaded dendritic cells to stimulate a CTL response can be measured by assaying the ability of the effector cells to lyse target cells. For example, the commonly-used europium release assay can be used. Typically, 5-10×106 target cells are labeled with europium diethylenetriamine pentaacetate for 20 minutes at 4° C. After several washes 104 europium-labeled target cells and serial dilutions of effector cells at an effector:target ratio ranging from 50:1 to 6.25:1 are incubated in 200 μl RPMI 1640 with 10% heat-inactivated fetal calf serum in 96-well plates. The plates are centrifuged at 500×g for 3 minutes and the incubated at 37° C. in 5% CO2 for 4 hours. A 50 μl aliquot of the supernatant is collected, and europium release is measured by time resolved fluorescence (Volgmann et al., *J. Immunol. Methods* 119:45-51, 1989).

A. Genetically Modified Dendritic Cells

Certain aspects of the embodiments concern dendritic cells that have been genetically modified. In some aspects, the genetic modification comprises introduction of an exogenous transgene in the cells, such as an inhibitory nucleic acid. In further aspects, the transgene may be a suicide gene, such as a gene encoding thymidine kinase, under the control of an inducible promoter. Thus, in some aspects, after stimulating an immune response, administered dendritic cells can be killed-off by induction of the promoter controlling expression of the suicide gene.

In further aspects, the genetic modification comprises a genomic deletion or insertion in the cell population. For example, one or more HLA gene may be disrupted to render the dendritic cells as an effective HLA match for a subject to be treated.

Further aspects of the embodiments concern dendritic cells that have been genetically modified, such as to reduce the expression of CTLA-4. In some aspects, the genetic modification comprises introduction of an exogenous inhibitory nucleic acid specific to CTLA-4. In certain aspects, the inhibitory nucleic acid is a RNA, such as a RNA that is expressed from a DNA vector in the dendritic cells. In further aspects, the inhibitory nucleic acid may be a siRNAs, dsRNA, miRNA or shRNA that is introduced in the dendritic cells. A detailed disclosure of such RNAs is provided above.

In further aspects, the genetic modification comprises a genomic deletion or insertion in the cell population that reduces CTLA-4. In other aspects, the dendritic cells comprises a hemizygous or homozygous deletion within the CTLA-4 gene. For example, in some aspects, one or both copies of the CTLA-4 gene of a dendritic cell can be completely or partially deleted, such that expression the CTLA-4 polypeptide is inhibited. In some aspects, modification the cells so that they do not express one or more CTLA-4 gene may comprise introducing into the cells an artificial nuclease that specifically targets the CTLA-4 locus. In various aspects, the artificial nuclease may be a zinc finger nuclease, TALEN, or CRISPR/Cas9. In various aspects, introducing into the cells an artificial nuclease may comprise introducing mRNA encoding the artificial nuclease into the cells.

V. COMBINATION THERAPIES

In order to increase the effectiveness of dendritic cell therapies which include dendritic cells transformed with nucleic acids generated by the embodiments, it may be desirable to combine these compositions with other agents effective in the treatment of the disease of interest.

As a non-limiting example, the treatment of cancer may be implemented with a primed dendritic cell composition of the present embodiments along with other anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the anti-cancer peptide or nanoparticle complex and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the dendritic cell composition and the other includes the second agent(s).

Treatment with a dendritic cell composition may precede or follow the other agent treatment by intervals ranging from minutes to weeks. In embodiments where the other agent and dendritic cell composition are applied separately to the subject, one would generally ensure that a significant period of time did not expire between the time of each delivery, such that the agent and the dendritic cell composition would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly where several days (e.g., 2, 3, 4, 5, 6 or 7 days) to several weeks (e.g., 1, 2, 3, 4, 5, 6, 7 or 8 weeks) lapse between the respective administrations.

Various combinations may be employed, where dendritic cell therapy is "A" and the secondary agent, such as radiotherapy, chemotherapy or anti-inflammatory agent, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

In certain embodiments, administration of dendritic cell therapy of the present embodiments to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of combination therapies. In some aspects a dendritic cell composition of the embodiments is administered (or formulated) in conjunction with a chemotherapeutic agent. For example, in some aspects the chemotherapeutic agent is a protein kinase inhibitor such as a EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitors. Nonlimiting examples of protein kinase inhibitors include Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, MK-2206, GSK690693, A-443654, VQD-002, Miltefosine, Perifosine, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016 or a mixture thereof.

Yet further combination chemotherapies include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above. In certain embodiments, the compositions provided herein may be used in combination with gefitinib. In other embodiments, the present embodiments may be practiced in combination with Gleevac (e.g., from about 400 to about 800 mg/day of Gleevac may be administered to a patient). In certain embodiments, one or more chemotherapeutic may be used in combination with the compositions provided herein.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Gene Therapy

In yet another embodiment, the secondary treatment is a gene therapy in which a therapeutic polynucleotide is administered before, after, or at the same time as the therapeutic composition. Viral vectors for the expression of a gene product are well known in the art, and include such eukaryotic expression systems as adenoviruses, adeno-associated viruses, retroviruses, herpesviruses, lentiviruses, poxviruses including vaccinia viruses, and papiloma viruses, including SV40. Alternatively, the administration of expression constructs can be accomplished with lipid based vectors such as liposomes or DOTAP:cholesterol vesicles. All of these methods are well known in the art (see, e.g. Sambrook et al., 1989; Ausubel et al., 1998; Ausubel, 1996).

D. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatments provided herein, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present embodiments may be used in conjunction with removal of superficial cancers, precancers, or incidental amounts of normal tissue. In some aspects, following tumor resection a dendritic cell composition of the embodiments is administered to lymphoid tissue that drained the previous site for the tumor.

VI. KITS

The technology herein includes kits for generating cDNA from mRNA in a sample, and the in vitro transcription of said cDNA. A "kit" refers to a combination of physical elements. For example, a kit may include, for example, one or more components including without limitation specific primers, enzymes, reaction buffers, an instruction sheet, and other elements useful to practice the technology described herein. These physical elements can be arranged in any way suitable for carrying out the invention.

The kit may further comprise a DNA polymerase, including for example, 029 polymerase, Bst polymerase, Taq polymerase, Vent polymerase, DNA polymerase I, the Klenow fragment of DNA polymerase I, 9° Nm Polymerase, T4 polymerase, T7 DNA polymerase, Pfu DNA polymerase, Q5® polymerase (New England Biolabs), or a RNA polymerase, and a reverse transcriptase. A mutant form of T7 phage DNA polymerase that lacks 3'-5' exonuclease activity, or a mixture thereof.

The kit may further comprise a RNA polymerase for in vitro transcription, including for example, E. coli RNA polymerase, SP6 RNA polymerase, T3 RNA polymerase, T7 RNA polymerase, or mutants thereof.

The components of the kits may be packaged either in aqueous media or in lyophilized form. The container means of the kits will generally include at least one vial, test tube, flask, bottle, syringe or other container means, into which a component may be placed, and preferably, suitably aliquoted (e.g., aliquoted into the wells of a microtiter plate). Where there is more than one component in the kit, the kit also will generally contain a second, third or other additional container into which the additional components may be separately placed. However, various combinations of components may be comprised in a single vial. The kits of the present invention also will typically include a means for containing the nucleic acids, and any other reagent containers in close confinement for commercial sale. Such containers may include injection or blow molded plastic containers into which the desired vials are retained.

A kit will also include instructions for employing the kit components as well the use of any other reagent not included in the kit. Instructions may include variations that can be implemented. It is contemplated that such reagents are embodiments of kits of the invention. Such kits, however, are not limited to the particular items identified above and may include any reagent used for the manipulation or characterization of the methylation of a gene.

The container means of the kits will generally include at least one vial, test tube, flask, bottle, or other container means, into which a component may be placed, and preferably, suitably aliquoted. Where there is more than one component in the kit, the kit also will generally contain additional containers into which the additional components may be separately placed. However, various combinations of components may be comprised in a container. The kits of the present invention also will typically include a means for packaging the component containers in close confinement for commercial sale. Such packaging may include injection or blow-molded plastic containers into which the desired component containers are retained.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Fresh tissue processing—Following surgical removal of the tumor, tumor tissue was weighed and sliced into small pieces (about 20 mg/piece or smaller). All pieces were placed in a 1.5 mL cryovial with 1 mL of an RNA stabilization solution (RNALATER™, Invitrogen). The cryovial containing the RNALATER™ and dissected tumor is then left at 4° C. overnight to prevent RNase activity. Following overnight incubation at 4° C., the cryovial containing the tissue in RNALATER™ solution was centrifuged at 10,000 RPM for 1 min at 4° C. After centrifugation, the supernatant was removed by pipetting, and the dissected pieces of tissues were weighed. 10% of the tissue was used for subsequent preparation of total RNA, while the remaining 90% was used for subsequent preparation of antigenic lysates.

Preparation of antigenic lysates—Dissected tumor tissue was added to a 15 mL conical tube and dilute to 100 mg/mL in sterile PBS. A homogenous suspension of tissue in PBS was then made using a handheld tissue homogenizer. The tube containing the homogenous suspension was then immersed in liquid nitrogen or a dry ice/ethanol bath to freeze the suspension. After freezing, the cell suspension was then incubated in a 55° C. water bath until it was completely thawed. The freeze thaw cycle was repeated two further times. Following the final thaw, to ensure sterility and complete cell death, the cell suspension was Gamma irradiated with >2500 Gy of radiation via a cesium irradiator. Lysates were then stored at −20° C. until further use.

Preparation of antigenic mRNA—Total RNA was isolated from tissue stabilized with RNALATER™ reagent using the RNEASY® mini kit (Qiagen cat #74104), which utilizes spin columns, or the TRIPURE® (Roche) method, which utilizes a guanidinium thiocyanate and phenol mixture, each according to the manufacturer's instructions.

RNeasy Total RNA preparation—600 µL of Buffer RLT was added to 30 mg of tissue and the resulting mixture was homogenized using a handheld tissue homogenizer. 600 µL of 70% ethanol was added to the lysate, and mixed by pipetting. 700 µL of the sample was transferred to a RNeasy spin column, and placed in a 2 mL collection tube. The sample was centrifuged for 1 min at 8,000×g. Following centrifugation, the flow-through was discarded. The remaining lysate was added to the spin column and was centrifuged again. Following centrifugation, the flow-through was discarded. 350 µL of buffer RW1 was added to the column and centrifuged. DNase I solution was prepared by adding 10 µL of DNase I stock solution to 70 µL of buffer RDD, followed by gentle mixing. 80 µL of DNase I solution was then added to the column and incubated at room temperature for 15 min. Following DNase I incubation, 350 µL of buffer RW1 was added to the column and the column was centrifuged for 1 min at 8000×g. Following centrifugation the flow-through was discarded. The membrane was then washed by the addition of another 700 µL of buffer RW1, and another 1 min centrifugation at 8000×g, followed by two 500 µl washes with buffer RPE, with two centrifugations at 8000×g. The membrane was then dried by centrifugation for 2 min. RNA was eluted into a new column by direct addition of 50 µl of pre-warmed nuclease free water to the membrane in the column, 1 minute of incubation, and centrifugation at 8000×g for 1 minute. In order to concentrate the RNA, the elution was performed a second time using the eluent. Total RNA was then quantified. Total RNA was stored at −80° C. for long term storage.

Guanidinium Thiocyanate/Phenol/Chloroform RNA Isolation—1 mL of guanidinium thiocyanate and phenol reagent (TRIpure™ reagent from Roche, Cat. NO. 11 667 157 001) was added for every 50 mg of tumor tissue and the resulting mixture was homogenized using a handheld tissue homogenizer. The homogenized mixture was then centrifuged at 13,000 RPM for 5 min at 4° C. to clear the homogenate. The supernatant from the homogenate was transferred to a new RNase free tube. To clear the supernatant, 400 uL of chloroform was added, and the mixture was mixed thoroughly by inversion. The supernatant/chloroform mixture was then incubated at room temperature for 5-10 min. The mixture was then centrifuged at 4500 RPM for 45 min or 12,000×g for 15 min at 4° C. in order to clear it. Following centrifugation, the resulting mixture is present in 3 phases: the organic phase, the interface, and the aqueous phase. The aqueous phase is collected by pipetting and transferred directly to a pre-chilled tube. 0.5 mL of isopropanol were added for every 1 mL of starting guanidinium thiocyanate and phenol reagent. The isopropanol/supernatant mixture was mixed gently and incubated at room temperature for 10 min. Following incubation, the RNA was pelleted by centrifugation at 4500 RPM for 45 min or 12000×G for 15 min at 4° C. The pelleted RNA was washed with 1 mL of 70% ethanol and centrifuged again. The supernatant was removed by pipetting and the pellet was allowed to air dry for 5-10 minutes on ice. The pellet was then dissolved in 100 uL of RNase free water, and incubated at 55° C. for 5 min. The concentration of total RNA was then measured. Total RNA was stored at −80° C. for long term storage. Prior to first strand synthesis, total RNA isolated using the guanidinium thiocyanate method was DNase treated by the addition of 1 uL of amplification grade DNase (Invitrogen Cat. No. 18068-015) to 4 ug of total RNA in 10× buffer diluted to 1×. DNase reaction was allowed to proceed for 15 minutes, and stopped by the addition of 1 uL of EDTA.

cDNA synthesis—For each sample and control, the following RNA/primer annealing mix was prepared in a sterile 0.2 mL PCR tube: 4 uL of a 10 uM solution of SEQ ID NO: 1 (VKWD oligo), 4 uL of a 10 uM solution of SEQ ID NO: 2 (CDS 64T+Oligo), 4 ug of sample RNA, and water to a total reaction volume of 19 uL. The solution was mixed and spun briefly in a microfuge to condense the solution to the bottom of the tube. The solution was then incubated at 72° C. for 2 min in a preheated thermocycler, and then cooled to 4° C. The sample was then stored on ice while the first strand synthesis master mix was prepared.

First strand synthesis master mixes were prepared to account for each reaction plus one no template control, and prepared from reagents in the Superscript® First Strand Synthesis Kit (Invitrogen Cat. No. 11904-018). The master mix contains, per sample: 4 uL of 10× First-Strand Buffer, 4 uL DTT (100 mM), 1 uL of RNase inhibitor (RNase Out™) 4 uL $MgCl_2$ (25 mM), 4 uL dNTP Mix (10 mM each of dATP, dGTP, dCTP, and dTTP), and 4 uL of Superscript® II Reverse Transcriptase, for a total volume of 21 uL per sample.

21 uL of first strand synthesis mastermix was added to each tube containing 19 ul of RNA/primer annealing mix. Each reaction, including the NTC, was incubated at 42° C. for 1 hour to synthesize the first strand of the cDNA. The first strand synthesis reaction was then collected by a brief centrifugation in a microcentrifuge and chilled on ice prior to second strand cDNA synthesis.

The second strand synthesis master mix was prepared by adding 100 uL FastStart™ high fidelity reaction buffer with MgCl2, 40 uL of 10 μmol/L CDS 64T+Oligo (SEQ ID NO: 2), 20 uL of 20 μmol/L Powerswitch T7 primer (SEQ ID NO: 3), 20 uL dNTP mix (10 mM each, dATP, dGTP, dCTP, dTTP), 20 uL of FastStart high fidelity enzyme, and 780 uL of water, for a total of 980 uL per sample. 20 uL of the first strand synthesis reaction was added to the second strand synthesis master mix. The resulting mixture was then split into 10 equal volumes of 100 uL each in 0.2 mL PCR tubes. Each of these reactions was then subjected to thermal cycling using the following program:

| | |
|---|---|
| 1x | 95° C. for 5 min |
| 11x | 95° C. for 30 s |
| | 65° C. for 30 s |
| | 67° C. for 6 min |
| 9x | 95° C. for 35 s |
| | 65° C. for 35 s |
| | 67° C. for 6 min 5 seconds |
| | For each additional cycle, the 67° C. |
| | extension increases by an additional 5 seconds, |
| | e.g. cycle 1 = 6:05, cycle 2 = 6:10, cycle 3 = 6:15, etc. |
| 1x | 67° C. for 7 min |
| Hold | 4° C. |

Double stranded cDNA was then purified using the Salt-ethabol precipitation method. Sodium acetate (3M) was added to the sample at a 1:10 vol:vol ratio, followed by a 2:1 vol:vol ratio of chilled 100% ethanol. The sample was mixed gently and then incubated at −20° C. for 1 hour. The mixture was then centrifuged at 13,000 RPM for 20 min to pellet the DNA. The supernatant was carefully pipetted off the pelleted DNA. The resulting pellet was then washed by adding 100 uL of chilled 70% ethanol and resuspended. The solution was then centrifuged for 10 min at 13,000 RPM, and the supernatant was pipetted off. The pellet was then air dried for 10 minutes before dissolving in 20 uL of nuclease free water. The concentration of the cDNA was measured by nanodrop.

In vitro transcription—In vitro transcription was performed using the AMPLISCRIBE™ T7-FLASH™ in vitro amplification kit (LUCIGEN™ Cat. No. ASF3257). 20 uL reaction volumes were prepared by adding, in the following order: X uL of RNase free water (X being the amount of water required to achieve 20 uL reaction volume); 1 ug of cDNA template; 2 uL of AMPLISCRIBE™ T7-FLASH™ 10× reaction buffer; 1.8 uL each of 100 mM ATP, CTP, GTP and UTP; 2 uL DTT; 0.5 uL of RIBOGUARD™ RNase inhibitor; and 2 uL of AMPLISCRIBE™ T7-FLASH™ Enzyme solution. The reaction was then incubated for 1 hr at 42° C. in a thermocycler. Following incubation, 1 uL of RNase-free DNase 1 was added, and the reaction was incubated at 37° C. for 15 min. The DNase treated in vitro transcription reaction was brought to 50 uL by addition of 29 uL of RNase free water. The in vitro transcription reaction was then purified by salt and ethanol precipitation and purification. 50 uL of 5 M ammonium acetate and 100 uL of ice cold 100% ethanol were added to the in vitro transcription reaction and mixed. The resulting mixture was then incubated for 1 hr at −20° C. After incubation, the mixture was centrifuged at 10,000×g for 15 min at 4° C. The supernatant was removed from the pellet by pipetting. The pellet was then washed with 100 uL of cold 70% ethanol and centrifuged again at 10,000×g for 15 min at 4° C. The supernatant was removed by pipetting and the pellet was allowed to air dry before resuspending in 50 uL of RNase free water.

Capping of uncapped in vitro transcription generated RNA—Capping of the RNA generated by in vitro transcription generated RNA was performed using the SCRIPT-CAP™ m7G Capping System and SCRIPTCAP™ 2'-O-Methyltransferase Kit (CELLSCRIPT™ Cat. Nos. C-SCCE0625 and C-SCMT0625) according to the manufacturer's instructions. Briefly, 50-60 ug in vitro transcribed uncapped RNA was added to RNase free water to a total volume of 67 uL. The diluted RNA was then incubated at 65° C. for 10 min to denature, and subsequently stored on ice. A capping master mix was prepared by adding 10 uL of 10× SCRIPTCAP™ Capping buffer, 10 uL of 10 mM GTP, 2.5 uL of 20 mM S-adenosyl methionine, 2.5 uL SCRIPT-GUARD™ RNase inhibitor, and 4 uL SCRIPTCAP™ 2'-O-methyltransferase, per sample. The capping reaction was assembled by adding 4 uL of the SCRIPTCAP™ capping enzyme to 29 uL of the capping master mix, and adding that mix to the heat denatured RNA. The capping reaction was allowed to proceed at 37° C. for 30 min. Capped RNA was purified by salt and ethanol precipitation and purification as above, and resuspended in 50 uL of RNase free water. To assess the quality of the capped mRNA, 1 ug of capped mRNA was run on a 50 mL, 1% agarose non-denaturing gel. The capped mRNA was stored at −80° C.

Antigenic lysate preparation—To generate MHC class II determinants, 1 mL of PBS per 100 mg of tissue was added to the isolated tissue fractions, and the tissues were disrupted using a POLYTRON® PT1200E tissue homogenizer (Kinematica, Inc., Bohemia, N.Y.). The homogenized tissue fractions were then subjected to three repetitive freeze-thaw cycles, cycling the homogenized mixtures between liquid nitrogen and a 55 degree C. water bath, and stored at −20° C.

Human (Decker et al., 2006; Decker et al., 2009) and wild type mouse (Konduri et al., 2013) dendritic cells were prepared, loaded, and matured as described. In vitro co-cultures were performed as described previously (Decker et al., 2006; Decker et al., 2009; Konduri et al., 2013).

IFNγ production by T cells co cultured with dendritic cells loaded with capped mRNA. Total PBMC in the co-culture were treated for 5 hours with 10 µg/ml brefeldin A (eBioscience). Cells were stained for surface markers with anti-CD3, anti-CD8, and anti-CD25 antibodies and then fixed/permeabilized for intracellular staining of IFN-γ using the Cytofix/Cytoperm Kit (BD Biosciences) according to the manufacturer's instructions.

Homologous antigenic loading leads to enhanced production of AIMp1 and retention of CTLA-4. Enhanced production of AIMp1 was demonstrated by Western blot. Enhanced retention of CTLA-4 was demonstrated by CTLA-4 western blot of cell culture supernatants (to determine release) and intracellular flow cytometry to determine retained CTLA-4 content. Histogram analysis of intracellular CTLA-4 is gated on the CD11c+CD80+CD83+CD86+ cell population.

Western blot analysis. Preparation of whole cell lysate: cells were lysed in 1% NP-40 lysis buffer containing protease inhibitor cocktail, phosphatase inhibitor cocktail 2 and phosphatase inhibitor cocktail 3 (all purchased from Sigma-Aldrich) on ice with vortexing every 10-15 minutes. Cell lysate was centrifuged at 14,000×g for 15 minutes and the cleared lysate was denatured with laemmli buffer (Bio-Rad) containing 5% β-mercaptoethanol (Bio-Rad) for 10 minutes. Denatured whole cell lysate samples were stored at −20° C. for further analysis. Electrophoreses and blotting: proteins samples were separated by SDS-gel electrophoreses (Invitrogen) with subsequent transfer to a 0.45 µm nitrocellulose membrane (Bio-Rad) for antibody probing. All blocking and antibody staining steps were carried out in 5% BSA (RPI, Grainger) in 1×TBST buffer (0.05% Tween-20). Western blotting chemiluminescent signal was detected with SUPERSIGNAL® West Femto Maximum Sensitivity Substrate (ThermoFisher Scientific) using a CHEMIDOC® XRS digital imaging system supported by Image Lab software version 2.0.1 (Bio-Rad). Densitometry was performed using Image Lab software.

Example 2—Results

RNA isolation from fresh tissue yields high quality RNA—To determine whether fresh or frozen tissue yielded higher quality RNA for downstream processing, total RNA was isolated from 30 mg of 3 different frozen tumor tissues or a single fresh tumor. As can be seen in FIG. 1, the RNA isolated from the three frozen tissues exhibits significant degradation, visible as a large smear in the lanes. Lane 4 has two clearly defined bands, indicating that the integrity of the RNA is high.

Figure 2:
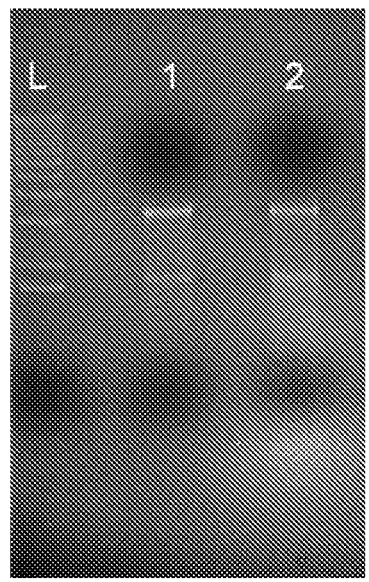
FIG. 2: Comparison of two different methods of RNA isolation. Pictured, RNA samples were run on a non-denaturing 1% agarose gel. Lane 1: RNA isolated from 30 mg of tumor tissue by column purification. Lane 2: RNA isolated from 30 mg of tumor tissue by guanidinium thiocyanate/phenol/chloroform purification.

Comparison of commercial RNA isolation methods—Total RNA was isolated from 30 mg of tumor tissue using either the RNEASY® mini kit (Qiagen) or using the TRIPURE® RNA isolation reagent (Roche), which is a guanidinium thiocyanate/phenol/chloroform based method. Both methods yielded high quality RNA as visible in FIG. 2, though the TRIPURE® method yielded 4.4-fold more RNA than the RNEASY® kit from the same input amount.

Figure 3:
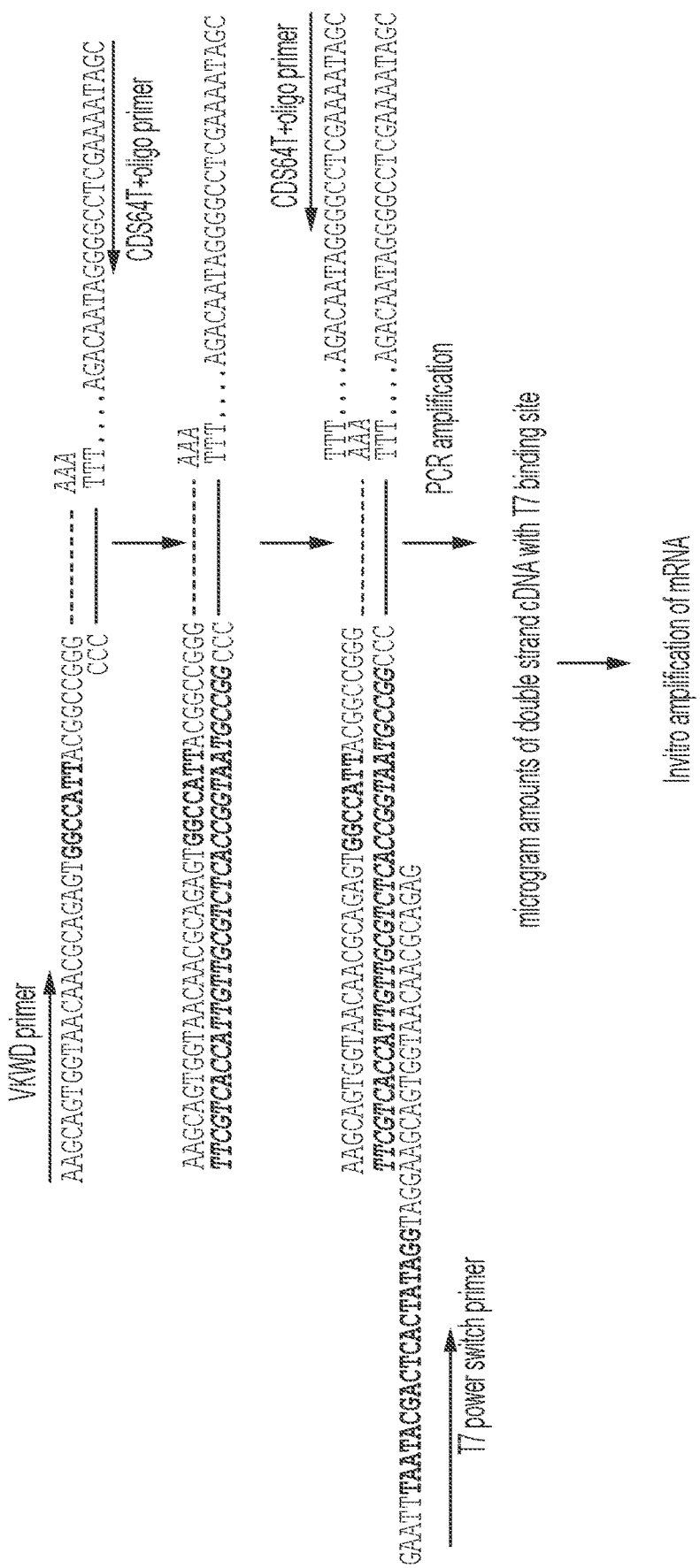
FIG. 3: Schematic showing the process of reverse transcription used in the present invention, indicating the primers used. VKWD primer has the nucleotide sequence of SEQ ID NO: 1. CDS64T+oligo primer has the nucleotide sequence of SEQ ID NO: 2. T7 power switch primer (SEQ ID NO:3) and comprises a T7 promoter sequence (SEQ ID NO:5). The power switch primer is used to prime the synthesis of the second strand of the cDNA, the primer comprising the nucleotide sequence of SEQ ID NO: 3. The polymerase extending the partial first strand of the cDNA with a sequence comprising SEQ ID NO:4.
Figure 4:
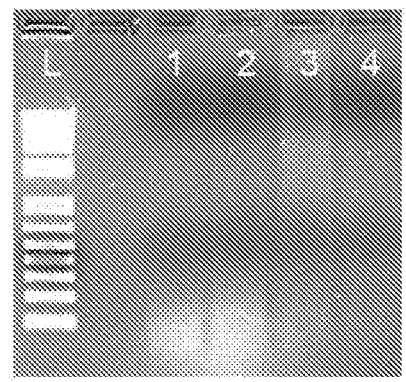
FIG. 4: Comparison of methods of reverse transcription followed by in vitro transcription. Pictured, 4 different protocols were used to generate in vitro transcribed RNA from identical starting material. Lane 1, uncapped transcripts generated by the Slagter-Jäger method (Slagter-Jäger et al., 2013). Lane 2, capped transcripts generated by the Slagter-Jäger method (Slagter-Jäger et al., 2013). Lane 3, uncapped RNA generated by the methods described herein. Lane 4, capped RNA generated by the methods described herein.

In Vitro Transcribed RNA from mRNA isolated from tumor cells—FIG. 3 depicts a schematic, including the primers, for the method used for reverse transcription of mRNA isolated from tumor cells, and subsequent in vitro transcription of the cDNA according to the present methods (see Example 1). Two different reverse transcription and in vitro transcription methods were compared (FIG. 4). Lanes 1 and 2 depict either uncapped RNA or capped RNA as prepared by the Slagter-Jäger method (Slagter-Jäger et al., 2013). Lanes 3 and 4 show either uncapped RNA or RNA prepared by the methods described herein. Previous methods show an enrichment of very small transcripts, while the methods described herein yielded a smear of RNA at larger molecular weights.

Figure 5:
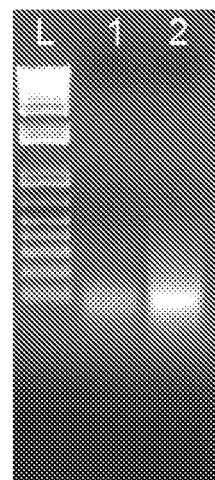
FIG. 5: Comparison of mRNA generated and capped by two different methods. 5 ug of in vitro transcribed mRNA was run on a 1% agarose, non-denaturing gel. Lane 1, mRNA generated by previous method (Slagter-Jäger et al., 2013) and capped post-transcription. Lane 2, mRNA generated by the present methods and capped co-transcriptionally.

Enrichment of small transcripts by co-transcriptional capping. In order to insure accurate representation of all transcripts, two methods were tested for capping of in vitro transcribed mRNA. FIG. 5 depicts an agarose gel of the capped RNA generated by each method. Lane 1 shows RNA post-transcriptionally capped, while Lane 2 shows RNA which was co-transcriptionally capped. Clearly, the transcript smear is much more evident in lane 2, in which the RNA was produced by the present methods and co-transcriptionally capped. Tables 1 and 2 show the concentrations, volume, and yields of products generated by the Slagter-Jäger method (Slagter-Jäger et al., 2013). Konduri/Decker Hybrid preparation is according to the present methods.

TABLE 1

In vitro transcribed RNA prepared from RNEASY® isolated total RNA.

| RNEASY® column | Concentration | Volume | Yield |
|---|---|---|---|
| RNA yield | 200 ng/ul | 90 ul | 18 ug |
| Argos method | | | |
| ds-cDNA | 20 ng/ul | 100 ul | 2 ug |
| uncapped mRNA | 2.8 ug/ul | 100 ul | 280 ug |
| capped mRNA | 2.0 ug/ul | 20 ul | 40 ug |
| co-transcribed capped mRNA | 90 ng/ul | 25 ul | 2.2 ug |
| Konduri/Decker Hybrid | | | |
| ds-cDNA | 47 ng/ul | 100 ul | 4.7 ug |
| uncapped mRNA | 3.0 ug/ul | 100 ul | 300 ug |
| capped mRNA | 2.5 ug/ul | 20 ul | 50 ug |
| co-transcribed capped mRNA | 2.0 ug/ul | 35 ul | 70 ug |

TABLE 2

In vitro transcribed RNA prepared from TRIPURE™ isolated total RNA.

| TRIPURE® method | Concentration | Volume | Yield |
|---|---|---|---|
| RNA yield | 2 ng/ul | 40 ul | 80 ug |
| Argos method | | | |
| ds-cDNA | 20 ng/ul | 120 ul | 2.4 ug |
| uncapped mRNA | 2.5 ug/ul | 100 ul | 250 ug |
| capped mRNA | 2.4 ug/ul | 30 ul | 72 ug |
| co-transcribed capped mRNA | 2.7 ng/ul | 30 ul | 81 ug |
| Konduri/Decker Hybrid | | | |
| ds-cDNA | 21 ng/ul | 120 ul | 2.5 ug |
| uncapped mRNA | 2.6 ug/ul | 100 ul | 260 ug |

TABLE 2-continued

In vitro transcribed RNA prepared from TRIPURE ™ isolated total RNA.

| TRIPURE ® method | Concentration | Volume | Yield |
|---|---|---|---|
| capped mRNA | 2.0 ug/ul | 40 ul | 80 ug |
| co-transcribed capped mRNA | 3.3 ug/ul | 60 ul | 198 ug |

Figure 6:
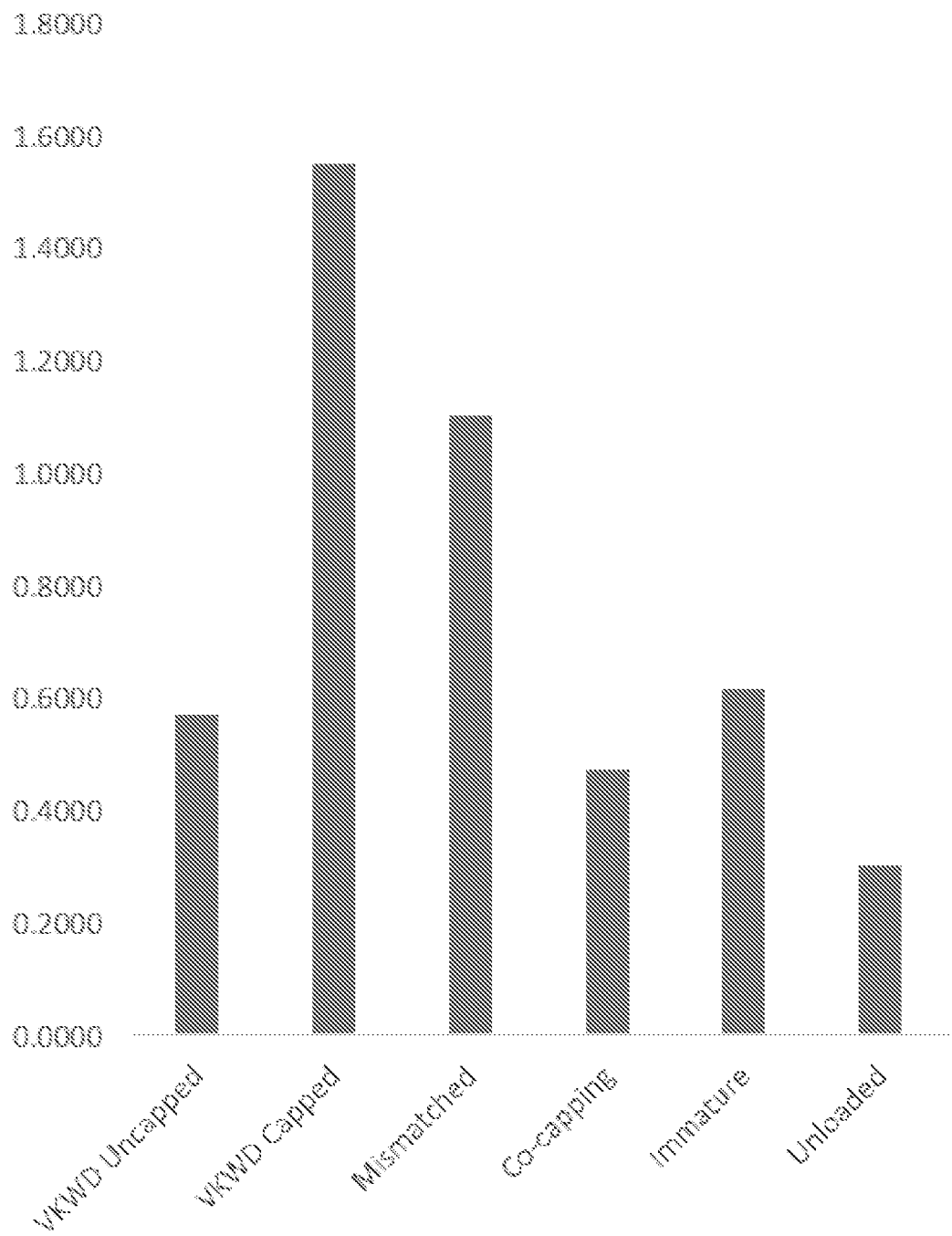
FIG. 6: IFNγ production is significantly enhanced by T cells cocultured with dendritic cells loaded with capped mRNA and lysates. Pictured, relative amounts of IFN-γ secretion as measured by ELISA for cells loaded with uncapped or capped mRNA generated by the previous method (Argos (Slagter-Jäger)) or the present methods (VKWD), and lysates, or with mismatched mRNA and lysates.

IFNγ production is enhanced by co-culture with loaded DCs—Dendritic cells were homologously loaded with antigenic lysate and mRNA prepared by the methods described herein, or heterologously loaded with prostate mRNA and pancreatic tumor lysate (mismatched). FIG. 6 shows relative IFNγ levels produced by T cells cocultured with the indicated dendritic cells. Dendritic cells loaded with capped RNA and antigenic lysate clearly stimulate IFNγ production, and does so better than dendritic cells loaded with uncapped RNA, or immature or unloaded dendritic cells.

Figure 7:
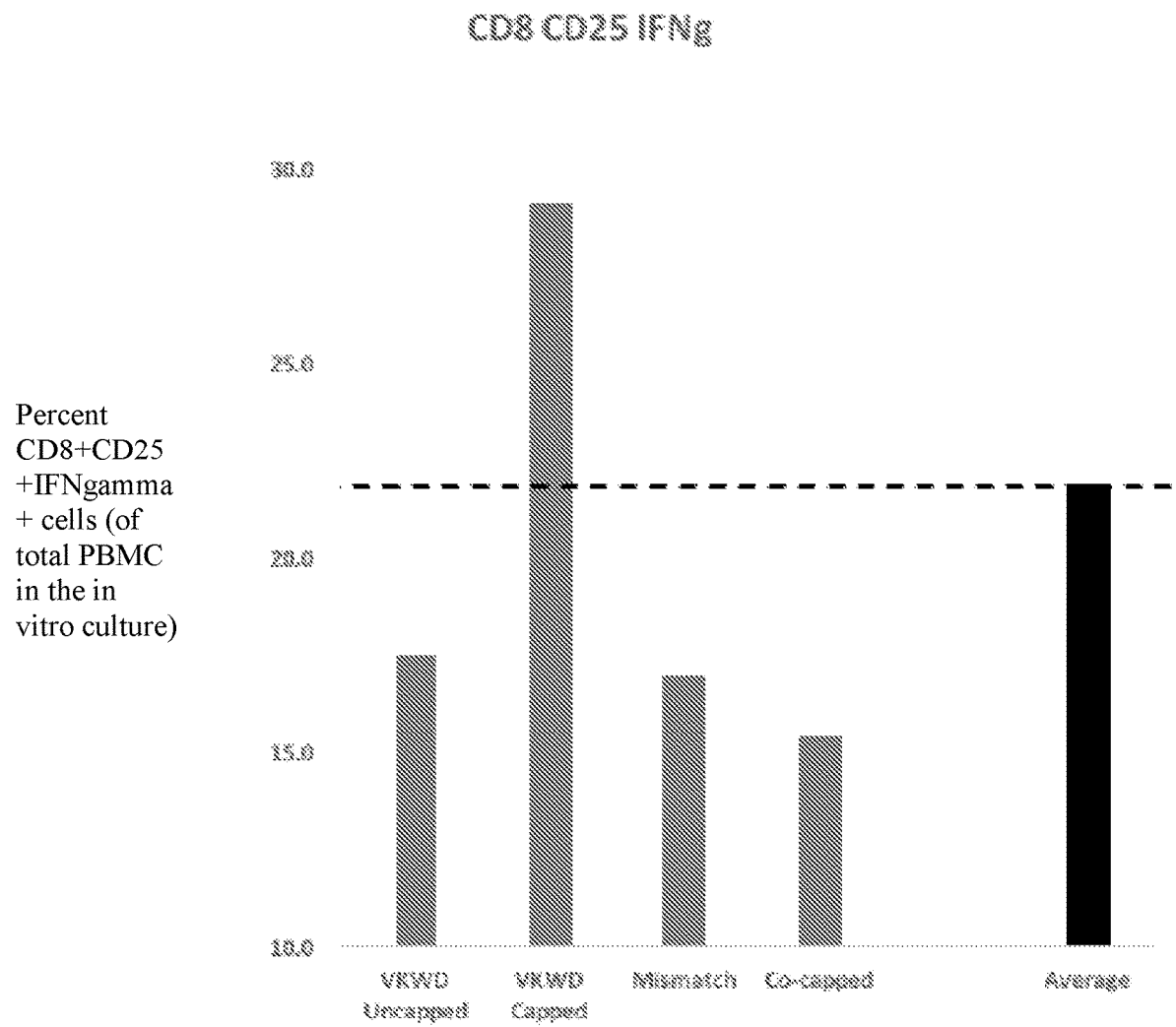
FIG. 7: Antigen specific CD8$^+$CD25$^+$ T cell production is enhanced when co-cultured with dendritic cells homologously loaded with capped mRNA and lysate. Pictured, flow cytometric analysis of T cells for antigen specific activation markers following re-stimulation with dendritic cells loaded with the mRNA shown below the data.

Co-culture with homologously loaded dendritic cells enhances antigen specific CD8$^+$CD25$^+$ T cells—FIG. 7 shows the results of flow cytometric analysis of CD8$^+$CD25$^+$ cells sorted for IFNγ levels, after co-culture with dendritic cells homologously loaded with either uncapped or capped mRNA produced by the methods described herein and lysate, or loaded with prostate mRNA and pancreatic tumor lysate (mismatched). Homologously loading lysate and mRNA produced by the methods described herein significantly enhances the levels of antigen specific CD8$^+$CD25$^+$ T cells.

Figure 8:
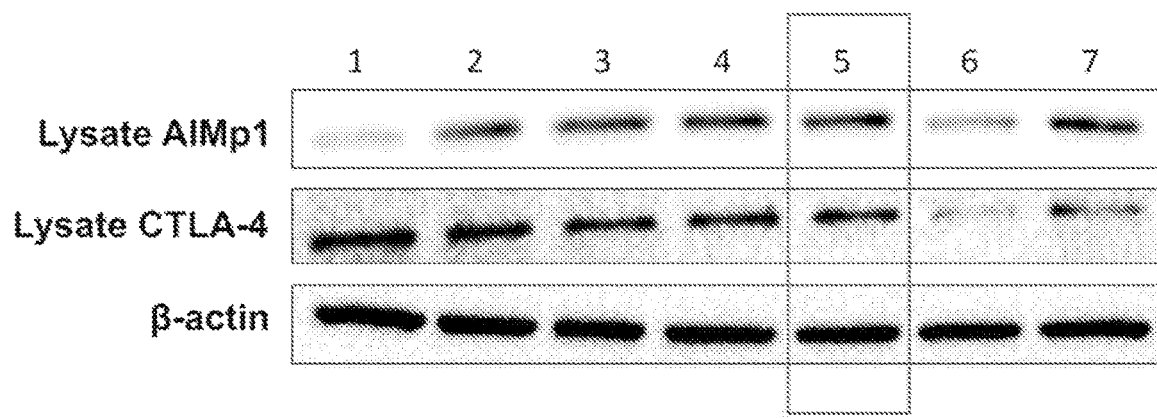
FIG. 8: Western blot analysis of dendritic cell lysates. Lane 1: unloaded dendritic cells. Lane 2: dendritic cells loaded with uncapped mRNA generated using the Slagter-Jäger method. Lane 3: dendritic cells loaded with capped mRNA generated using the Slagter-Jäger method. Lane 4: dendritic cells loaded with uncapped mRNA generated using the methods described herein. Lane 5: dendritic cells loaded with capped mRNA generated using the methods described herein. Lane 6: dendritic cells loaded with mismatched mRNA and lysate. Lane 7: dendritic cells loaded with mRNA generated using the methods described herein and capped co-transcriptionally.
Figure 9:
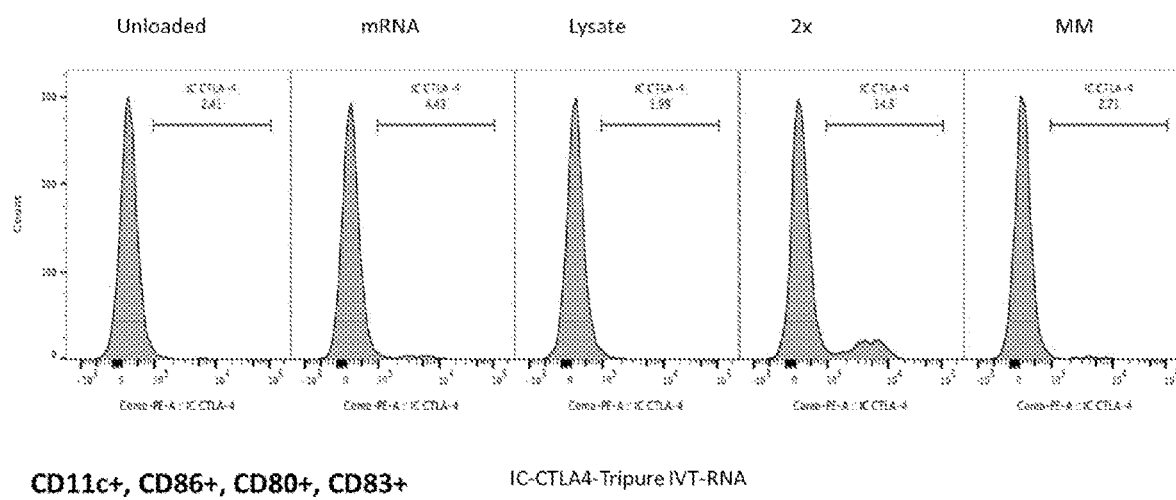
FIG. 9: Homologous antigenic loading with in vitro transcribed and amplified mRNA leads to enhanced retention of CTLA4. Pictured are flow cytometric analyses of dendritic cells either unloaded, or loaded with the indicated: mRNA, Lysate, 2× (mRNA and Lysate), and MM (mismatched mRNA and lysate).
Figure 10:
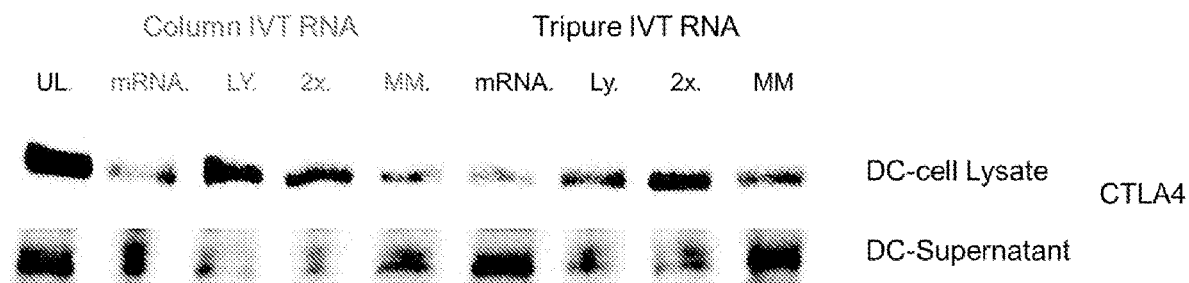
FIG. 10: Enhanced retention and reduced release of CTLA4 from the homologously loaded dendritic cells. Pictured are western blots detecting CTLA4 in the supernatant or the lysate of dendritic cell cultures. Dendritic cells were either unloaded (UL) or loaded with mRNA, lysate, both, or mismatched mRNA and lysate. mRNA was isolated by either a column based method or guanidinium thiocyanate/phenol/chloroform method.

Homologous antigenic loading enhances production of AIMp1 and retention of CTLA4—Dendritic cells were evaluated for AIMp1 production and CTLA4 retention after either homologous antigenic loading or heterologous antigenic loading (mismatch). FIG. 8 shows a western blot for AIMp1 and CTLA-4 in the lysates with β-actin provided as a control. Homologous antigenic loading with capped mRNA made by the methods provided herein have increased amounts of AIMp1 and a high amount of intracellular CTLA-4, as can be seen in lane 5. To confirm this, flow cytometry was performed on dendritic cells either unloaded, loaded with just mRNA, just lysate, both, or mismatched antigens. FIG. 9 shows that CTLA4 retention is significantly enhanced in CD11c+CD80+CD83+CD86+ cells loaded with both the mRNA and homologous antigenic lysate. Further confirming enhanced CTLA4 retention by cells homologously loaded with antigenic lysate and mRNA generated by the methods provided herein, dendritic cell lysates and supernatant were probed for CLTA4 by western blot (FIG. 10). Loading with antigenic lysate and mRNA prepared by either method decreased the amount of CTLA4 present in the supernatant, indicating enhanced retention.

Figure 11:
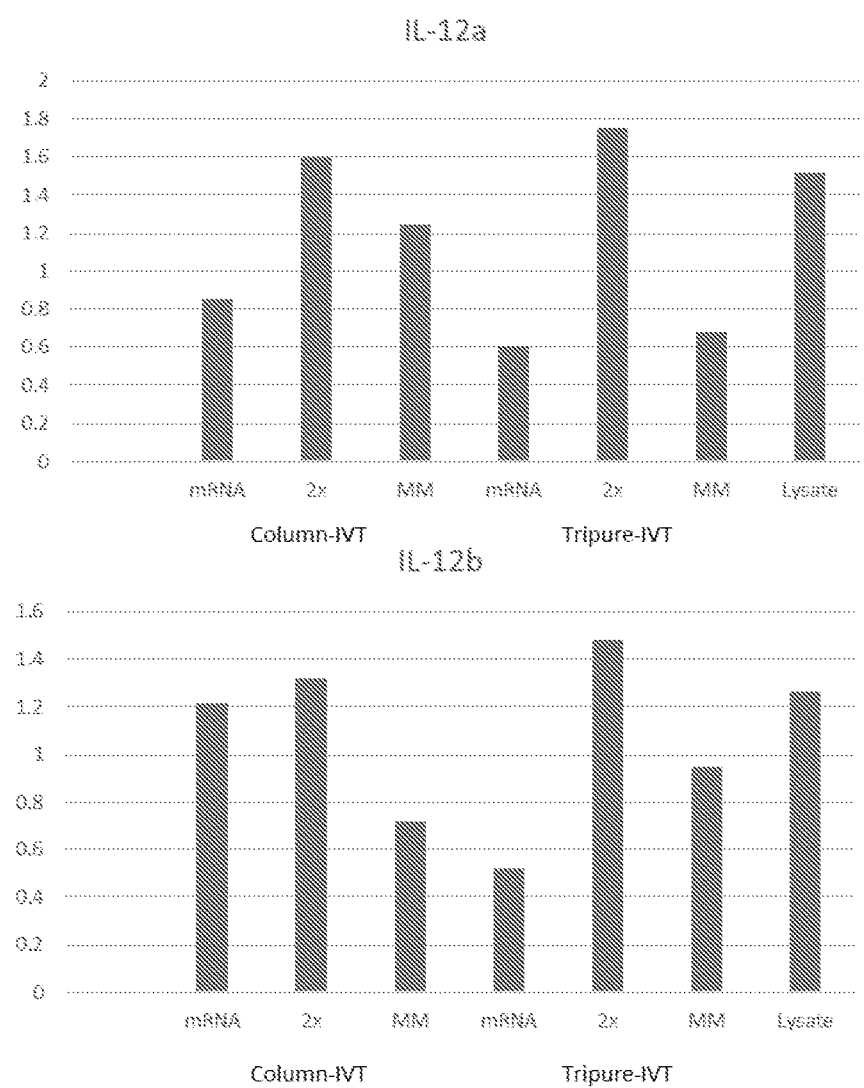
FIG. 11: IL-12 transcript levels are elevated in dendritic cells homologously loaded with lysates and in vitro transcribed mRNA. Shown are IL-12a and IL-12b levels as detected by ELISA for dendritic cells loaded with the indicated RNA and/or lysate. The left axis indicates arbitrary transcriptional units normalized to unloaded control DC and set at 1.0.
Figure 12:
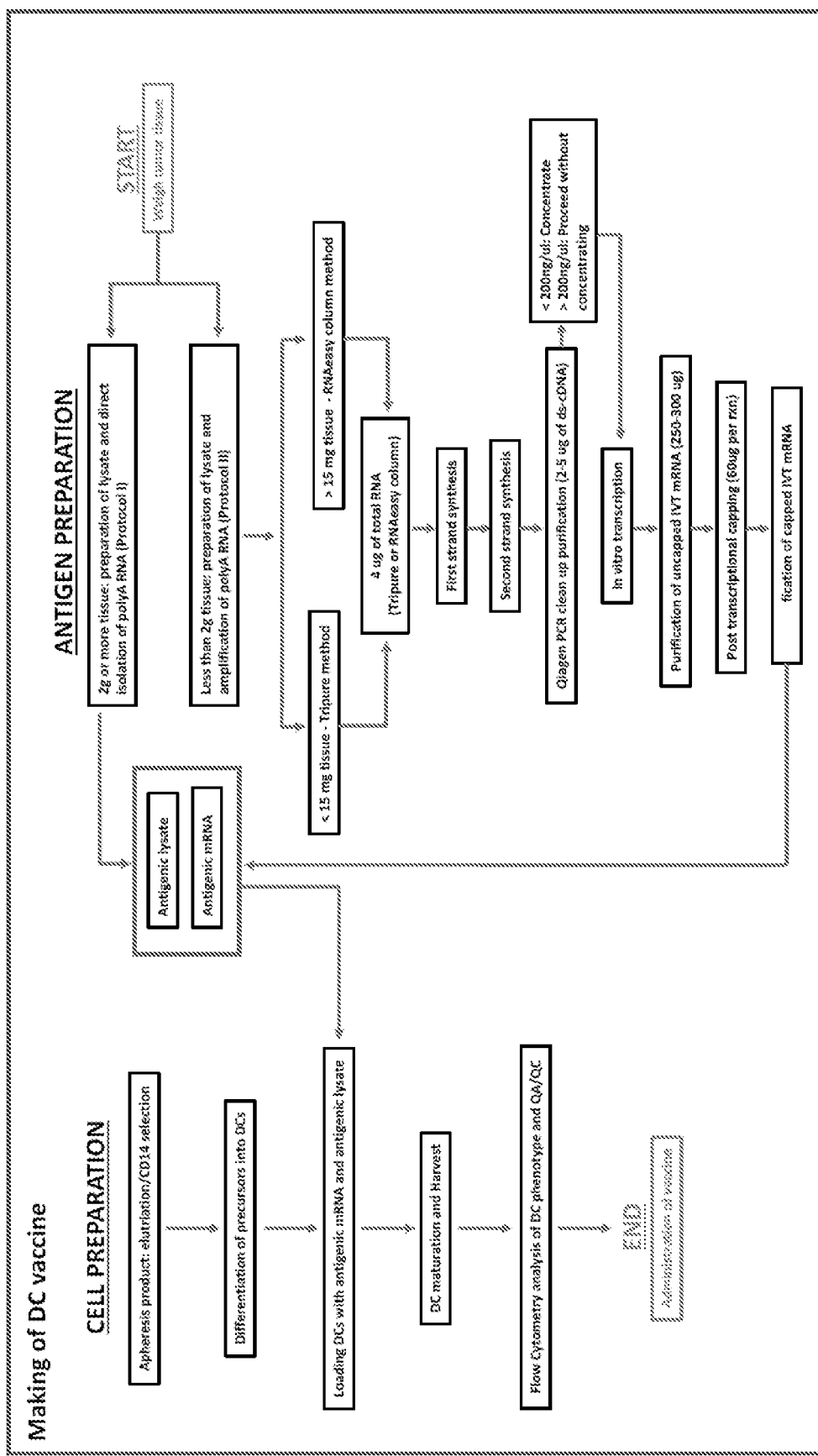
FIG. 12: Flow chart describing the preparation of a dendritic cell vaccine.

Homologous antigenic loading increases IL-12 transcripts in dendritic cells—Dendritic cells were evaluated for IL-12a and IL-12b production by RT-qPCR. As can be seen in FIG. 11, antigenic loading with both lysate and mRNA generated by the methods provided herein (TRIpure-IVT) increases both IL-12 transcripts better than loading with just lysate, mRNA, or heterologous loading, as well as increasing IL-12 transcript production better than loading with mRNA prepared by previous methods (Column-IVT).

Example 3—Additional Studies with Amplified mRNAs

Figure 13A:
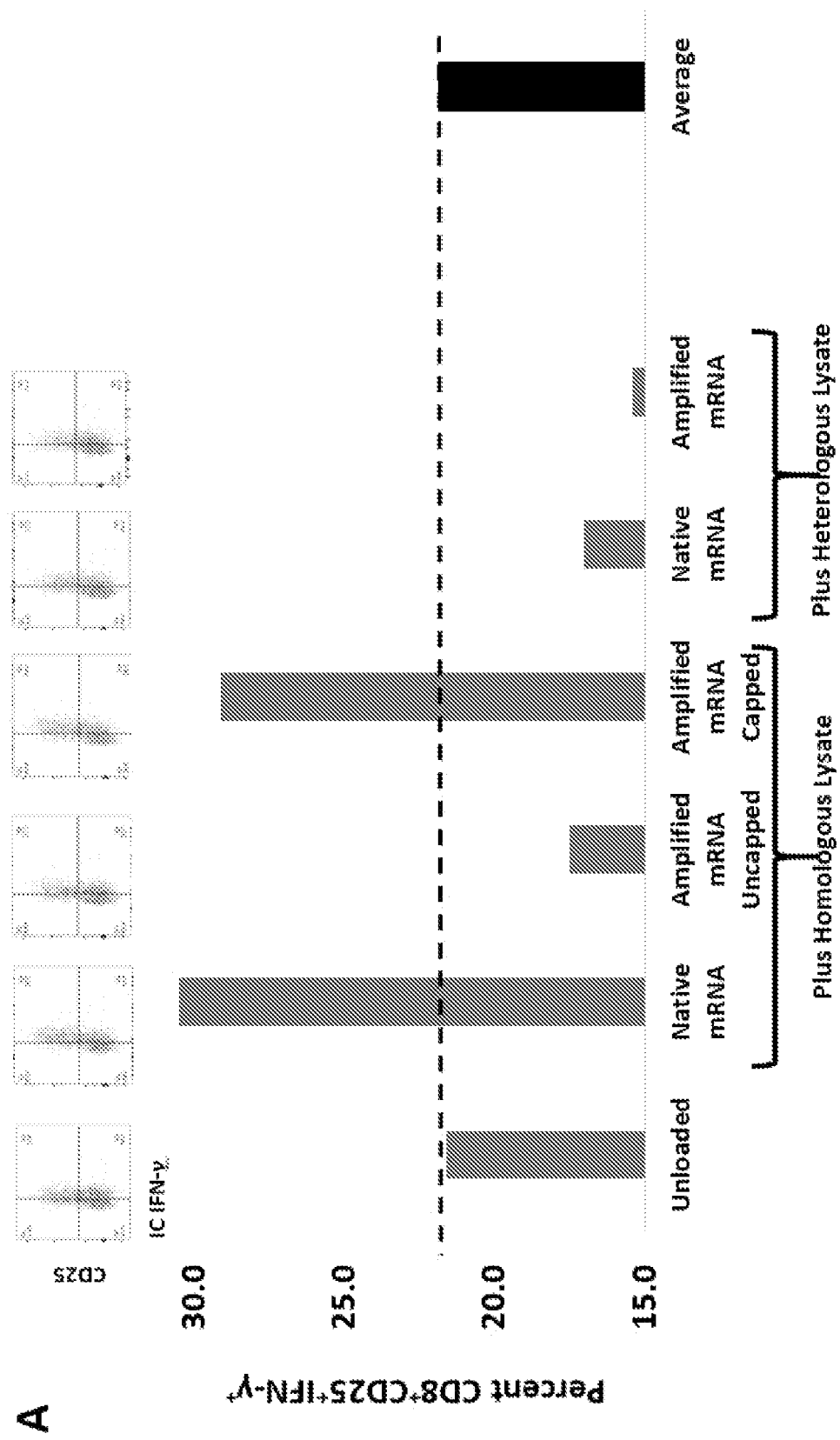
FIG. 13A-B: Amplified mRNA generates TH1 immune responses in vitro with the same efficiency as native poly-A mRNA when loaded into DC with homologous lysate. (A) Monocyte-derived human DC were loaded with a) native poly A tumor mRNA and homologous/heterologous lysate or 2) capped IVT-amplified mRNA and homologous/heterologous lysate. DC were then cocultured with T cells and the percent of activated CD8+CD25+Ifng+ cells were analyzed by flow. T cells cocultured with unloaded DC or DC loaded with uncapped mRNA served as controls. (B) DC loaded with various combinations of poly A mRNA or IVT-amplified mRNA and homologous or heterologous cell lysates were matured for 48 hours, and intracellular CTLA4 levels were analyzed by flow cytometry. Singly loaded and unloaded DCs serve as controls. Upregulation of intracellular CTLA-4 is indicative of increased retention and therefore reduced secretion. UL-unloaded DC, uncapped mRNA-DC loaded with uncapped IVT mRNA, mRNA-DC loaded with poly A mRNA, lysate-DC loaded with lysate, 2× w/uncapped-DC loaded with uncapped IVT mRNA and homologous lysate, 2× capped-DC loaded with capped IVT mRNA and homologous lysate, MM uncapped-DC loaded with uncapped IVT mRNA and heterologous lysate, MM capped-DC loaded with capped IVT mRNA and heterologous lysate.
Figure 13B:
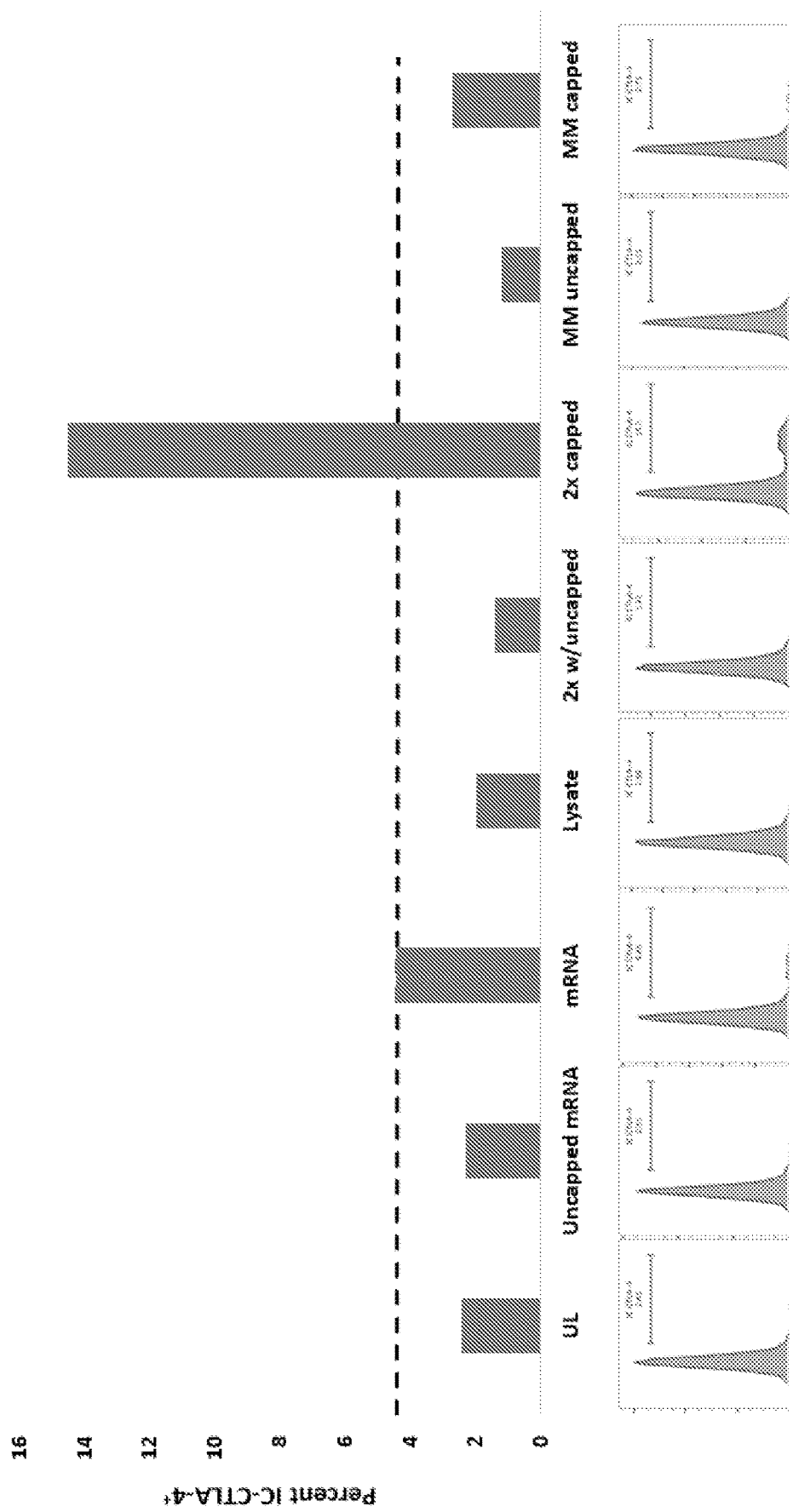

Additional studies were performed demonstrating that amplified mRNA generates TH1 immune responses in vitro with the same efficiency as native poly-A mRNA when loaded into DC with homologous lysate. For example, results shown in FIG. 13A show monocyte-derived human DC that were loaded with a) native poly A tumor mRNA and homologous/heterologous lysate or 2) capped IVT-amplified mRNA and homologous/heterologous lysate. DC were then cocultured with T cells and the percent of activated CD8+CD25+Ifng+ cells were analyzed by flow. T cells cocultured with unloaded DC or DC loaded with uncapped mRNA served as controls. FIG. 13B shows results with DC loaded with various combinations of poly A mRNA or IVT-amplified mRNA and homologous or heterologous cell lysates were matured for 48 hours, and intracellular CTLA4 levels were analyzed by flow cytometry. Singly loaded and unloaded DCs serve as controls. Upregulation of intracellular CTLA-4 is indicative of increased retention and therefore reduced secretion. UL-unloaded DC, uncapped mRNA-DC loaded with uncapped IVT mRNA, mRNA-DC loaded with poly A mRNA, lysate-DC loaded with lysate, 2× w/uncapped-DC loaded with uncapped IVT mRNA and homologous lysate, 2× capped-DC loaded with capped IVT mRNA and homologous lysate, MM uncapped-DC loaded with uncapped IVT mRNA and heterologous lysate, MM capped-DC loaded with capped IVT mRNA and heterologous lysate.

Methods of the embodiments were able to amplify sufficient amounts of mRNA for use in stimulating an immune response from very small amounts of starting tissue. Results presented in Table 3 below shows the amount to RNA that could be generated from a variety of starting samples.

TABLE 3

Additional preparation of nucleic acids from tumor tissues by the methods of the embodiments.

| Tumor Type | Experiment | Tissue in mg | Total RNA | Template Total RNA | ds-cDNA | Template ds-cDNA | Capped IVT |
|---|---|---|---|---|---|---|---|
| Primary PDAC | 1 | 15 mg | 1.4 ug | 1.4 ug | 41.0 ug | 1 ug | 45 ug |
| Primary PDAC | 2 | 10 mg | 3.6 ug | 3.0 ug | 32.6 ug | 1 ug | 94 ug |
| Primary Prostate | 3 | 20 mg | 1.4 ug | 1.3 ug | 22.6 ug | 2 × 1 ug | 300 ug |
| Primary PDAC | 4 | 10 mg | 3.0 ug | 3.0 ug | 45.0 ug | 1 ug | 70 ug |
| Dermal metastasis from HR-positive breast carcinoma | 5 | 80 mg | 66.7 ug | 5 ug | 22.0 ug | 2 × 2 ug | 360 ug |
| Pleural cavity metastsis from poorly-differentiated head and neck sarcoma | 6 | 60 mg | 30.0 ug | 4 ug | 60.0 ug | 2 × 5 ug | 270 ug |

TABLE 3-continued

Additional preparation of nucleic acids from tumor tissues by the methods of the embodiments.

| Tumor Type | Experiment | Tissue in mg | Total RNA | Template Total RNA | ds-cDNA | Template ds-cDNA | Capped IVT |
|---|---|---|---|---|---|---|---|
| Bone metastasis from esophageal adenocarcinoma | 7 | 20 mg | 4.0 ug | 4 ug | 21.3 ug | 2 × 2.5 ug | 240 ug |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Slagter-Jäger et al., "Evaluation of RNA Amplification Methods to Improve DC Immunotherapy Antigen Presentation and Immune Response," *Mol Ther Nucleic Acids*, 2(5): e91, 2013.

Decker W K, Xing D, Li S, et al., Double loading of dendritic cell MHC class I and MHC class II with an AML antigen repertoire enhances correlates of T-cell immunity in vitro via amplification of T-cell help, *Vaccine*, 2006, vol. 24 (pg. 3203-3216)

William K. Decker, et al., Th-1 polarization is regulated by dendritic-cell comparison of MHC class I and class II antigens *Blood* (2009) 113 (18): 4213-4223.

Vanaja Konduri, et al., Modeling Dendritic Cell Vaccination for Influenza Prophylaxis: Potential Applications for Niche Populations, *The Journal of Infectious Diseases*, Volume 207, Issue 11, 1 Jun. 2013, Pages 1764-1772

What is claimed is:

1. An in vitro method for preparing antigen-primed human dendritic cells for use in eliciting an immune response, the method comprising
   a) preparing an RNA by transcribing a cDNA synthesized from an mRNA, the RNA prepared by a method comprising:
      i) in an in vitro reaction mixture, hybridizing a first primer to the mRNA, wherein the first primer comprises both SEQ ID NO: 2 and a poly(T) sequence whereby the first primer anneals to the mRNA;
      ii) extending the first primer with a reverse transcriptase that has terminal transferase and template switching activity to generate a partial first cDNA strand with an oligo(C) overhang;
      iii) hybridizing a second primer comprising SEQ ID NO: 1 to the oligo(C) overhang of the partial first cDNA strand;
      iv) extending the partial first cDNA strand in the 3' direction from the oligo(C) overhang using the second primer as a template, thereby generating a first cDNA strand;
      v) hybridizing a third primer that comprises an RNA promoter to the first cDNA strand;
      vi) extending the third primer to generate a second cDNA strand, thereby generating a double stranded cDNA; and
      vii) synthesizing RNA from the double stranded cDNA; and
   b) priming the human dendritic cell with the synthesized RNA to provide the antigen-primed human dendritic cells for use in eliciting an immune response.

2. The method of claim 1, wherein the mRNA is from tumor cells.

3. The method of claim 2, wherein the mRNA is from a lysate of the tumor cells.

4. The method of claim 3, wherein the tumor cell lysate comprises a tumor antigen with an epitope having a sequence that overlaps a minimum of 5 amino acids with the sequence of the nucleic acid encoding one or more antigens.

5. The method of claim 1, wherein the mRNA is from a cell of an individual having an autoimmune disease.

6. The method of claim 1, wherein the mRNA is from a cell of an individual having an infectious disease.

7. The method of claim 1, wherein the RNA promoter is a T7 promoter.

8. The method of claim 1, wherein the third primer comprises the sequence of SEQ ID NO: 3.

9. The method of claim 1, wherein the mRNA, first primer, second primer and reverse transcriptase are comprised in the reaction mixture such that steps i) through iv) are carried out at the same time.

10. The method of claim 1, wherein the double stranded cDNA is amplified before synthesizing the RNA in step vii).

11. The method of claim 1, wherein the second primer consists of SEQ ID NO: 1.

12. The method of claim 1, wherein the method further comprises capping the RNA produced in step h).

13. The method of claim 1, further comprising administering the antigen-primed human dendritic cells to a human individual.

* * * * *

UNITED STATES PATENT AND TRADEMARK OFFICE
CERTIFICATE OF CORRECTION

PATENT NO. : 11,781,178 B2
APPLICATION NO. : 16/772682
DATED : October 10, 2023
INVENTOR(S) : William K. Decker and Vanaja Konduri It is certified that error appears in the above-identified patent and that said Letters Patent is hereby corrected as shown below:

In the Claims

Column 32, Line 49, Claim 12, delete "step h)" and insert --step vii)-- therefor.

Signed and Sealed this
Twenty-first Day of November, 2023

Katherine Kelly Vidal
*Director of the United States Patent and Trademark Office*

SEQUENCE LISTING

<160> NUMBER OF SEQ ID NOS: 5

<210> SEQ ID NO 1
<211> LENGTH: 39
<212> TYPE: DNA
<213> ORGANISM: Artificial sequence
<220> FEATURE:
<223> OTHER INFORMATION: Synthetic primer

<400> SEQUENCE: 1
aagcagtggt aacaacgcag agtggccatt acggccggg            39

<210> SEQ ID NO 2
<211> LENGTH: 25
<212> TYPE: DNA
<213> ORGANISM: Artificial sequence
<220> FEATURE:
<223> OTHER INFORMATION: Synthetic primer

<400> SEQUENCE: 2
cgataaaagc tccggggata acaga            25

<210> SEQ ID NO 3
<211> LENGTH: 50
<212> TYPE: DNA
<213> ORGANISM: Artificial sequence
<220> FEATURE:
<223> OTHER INFORMATION: Synthetic primer

<400> SEQUENCE: 3
gaatttaata cgactcacta taggtaggaa gcagtggtaa caacgcagag            50

```
<210> SEQ ID NO 4
<211> LENGTH: 36
<212> TYPE: DNA
<213> ORGANISM: Artificial sequence
<220> FEATURE:
<223> OTHER INFORMATION: Synthetic primer

<400> SEQUENCE: 4
ttcgtcacca ttgttgcgtc tcaccggtaa tgccgg                         36

<210> SEQ ID NO 5
<211> LENGTH: 18
<212> TYPE: DNA
<213> ORGANISM: Artificial sequence
<220> FEATURE:
<223> OTHER INFORMATION: Synthetic primer

<400> SEQUENCE: 5
taatacgact cactatag                                             18
```